United States Patent
Stango et al.

(10) Patent No.: US 10,603,002 B2
(45) Date of Patent: Mar. 31, 2020

(54) PIVOTING PADDLE APPARATUS FOR MAMMOGRAPHY/TOMOSYNTHESIS X-RAY SYSTEM

(71) Applicant: HOLOGIC, INC., Bedford, MA (US)

(72) Inventors: Timothy Stango, Sandy Hook, CT (US); Loren Niklason, North Tetonia, ID (US)

(73) Assignee: Hologic, Inc., Marlborough, MA (US)

( * ) Notice: Subject to any disclaimer, the term of this patent is extended or adjusted under 35 U.S.C. 154(b) by 278 days.

(21) Appl. No.: 15/524,852

(22) PCT Filed: Nov. 3, 2015

(86) PCT No.: PCT/US2015/058782
§ 371 (c)(1),
(2) Date: May 5, 2017

(87) PCT Pub. No.: WO2016/073445
PCT Pub. Date: May 12, 2016

(65) Prior Publication Data
US 2017/0340303 A1 Nov. 30, 2017

Related U.S. Application Data

(60) Provisional application No. 62/076,880, filed on Nov. 7, 2014.

(51) Int. Cl.
*A61B 6/00* (2006.01)
*A61B 6/04* (2006.01)
(Continued)

(52) U.S. Cl.
CPC .............. *A61B 6/502* (2013.01); *A61B 6/025* (2013.01); *A61B 6/0414* (2013.01);
(Continued)

(58) Field of Classification Search
CPC ..... A61B 6/025; A61B 6/4291; A61B 6/0414; A61B 6/4435; A61B 6/502; A61B 90/17
See application file for complete search history.

(56) References Cited

U.S. PATENT DOCUMENTS

| 3,971,950 A | 7/1976 | Evans et al. |
|---|---|---|
| 4,496,557 A | 1/1985 | Malen |

(Continued)

FOREIGN PATENT DOCUMENTS

| KR | 10-2011-0089446 A | 8/2011 |
|---|---|---|
| WO | 2010/028208 A1 | 3/2010 |

OTHER PUBLICATIONS

European Extended Search Report in Application 15857678.5, dated Jun. 26, 2018, 8 pages.
(Continued)

*Primary Examiner* — Chih-Cheng Kao

(57) ABSTRACT

A system has an imaging system housing and an x-ray source, thereto, a compression arm assembly housing, a support, and a detector. A paddle is disposed between the support and the x-ray source. A bottom surface of the paddle at least partially defines a plane. When in a rest position, the plane is substantially parallel to the support. A pivot mechanism connects the paddle to the compression arm assembly housing. The pivot mechanism defines an axis of rotation substantially parallel to a sagittal plane of the patient. The pivot mechanism has at least one biasing element for biasing the paddle into the rest position.

10 Claims, 19 Drawing Sheets

(51) Int. Cl.
*A61B 90/17* (2016.01)
*A61B 6/02* (2006.01)
(52) U.S. Cl.
CPC ............ *A61B 6/4435* (2013.01); *A61B 90/17* (2016.02); *A61B 6/4291* (2013.01)

(56) References Cited

U.S. PATENT DOCUMENTS

| | | | |
|---|---|---|---|
| 5,051,904 | A | 9/1991 | Griffith |
| 5,359,637 | A | 10/1994 | Webber |
| 5,506,877 | A * | 4/1996 | Niklason ................ A61B 6/502 378/208 |
| 5,706,327 | A * | 1/1998 | Adamkowski ....... A61B 6/0414 378/208 |
| 6,289,235 | B1 | 9/2001 | Webber |
| 6,647,092 | B2 | 11/2003 | Eberhard |
| 7,831,296 | B2 | 11/2010 | Defreitas |
| 8,175,219 | B2 | 5/2012 | DeFreitas et al. |
| 2001/0038861 | A1 | 11/2001 | Hsu |
| 2002/0061090 | A1 * | 5/2002 | Lindstrom ........... A61B 6/0414 378/37 |
| 2004/0066882 | A1 | 4/2004 | Eberhard |
| 2004/0066884 | A1 | 4/2004 | Claus |
| 2004/0066904 | A1 | 4/2004 | Eberhard |
| 2005/0008117 | A1 * | 1/2005 | Livingston ........... A61B 6/0414 378/37 |
| 2005/0063509 | A1 | 3/2005 | DeFreitas et al. |
| 2005/0113681 | A1 | 5/2005 | DeFreitas et al. |
| 2008/0080668 | A1 | 4/2008 | Kashiwagi |
| 2012/0277625 | A1 * | 11/2012 | Nakayama ........... A61B 6/0414 600/567 |

OTHER PUBLICATIONS

International Search Report and Written Opinion of the International Searching Authority for corresponding International Patent Application No. PCT/US2015/058782 dated Feb. 17, 2016, 14 pgs.
Digital Clinical Reports, Tomosynthesis (GE Brochure 98-5493, Nov. 1998), 8 pgs.
Grant, D.G., "Tomosynthesis: a three-dimensional imaging technique", IEEE Trans. Biomed. Engineering, vol. BME-19, #1, (Jan. 1972), pp. 20-28.
U.S. Appl. No. 60/628,516 entitled "Matching geometry generation and display of mammograms and tomosynthesis images", filed Nov. 15, 2004, 20 pgs.
PCT International Preliminary Report on Patentability in International Application PCT/US2015/058782, dated Jun. 18, 2017, 10 pgs.

* cited by examiner

PIVOTING PADDLE APPARATUS FOR MAMMOGRAPHY/TOMOSYNTHESIS X-RAY SYSTEM

This application is a National Stage Application of PCT/US2015/058782, filed Nov. 3, 2015, which claims priority to U.S. Provisional Patent Application No. 62/076,880, filed Nov. 7, 2014, the disclosures of which are hereby incorporated by reference herein in their entireties. To the extent appropriate, a claim of priority is made to each of the above disclosed applications.

INTRODUCTION

X-ray mammography has long been a screening modality for breast cancer and other lesions, and also has been relied on for diagnostic and other purposes. For many years, the breast image was recorded on x-ray film but digital x-ray image receptors have come into use, as in the Selenia® mammography system available from Hologic Inc. of Bedford, Mass. For mammograms, a cone-shaped or pyramid-shaped x-ray beam passes through the compressed breast and forms a two-dimensional projection image. Any one of a number of orientations can be used, such as cranial-caudal (CC) or MLO (mediolateral-oblique) orientation. More recently, breast x-ray tomosynthesis has come into use. The technology typically involves taking two-dimensional (2D) projection images of the immobilized breast at each of a number of angles of the x-ray beam relative to the breast and processing the resulting x-ray measurements to reconstruct images of breast slices that typically are in planes transverse to the x-ray beam axis, such as parallel to the image plane of a mammogram of the same breast. Mammography systems can also be used in interventional procedures, such as biopsy, by adding a biopsy station (for example, the Stereo-Loc II® Upright Stereotactic Breast Biopsy System, which is available from Hologic, Inc.). The patents, applications, brochures, and article cited above are hereby incorporated by reference in this patent specification as though fully set forth herein.

In clinical use, it can be desirable for a number of reasons to assess both tomosynthesis images and conventional mammograms of the patient's breasts. For example, the decades of conventional mammograms have enabled medical professionals to develop valuable interpretation expertise. Mammograms may offer good visualization of microcalcifications, and can offer higher spatial resolution compared with tomosynthesis. Tomosynthesis images may have different desirable characteristics—e.g., they may offer better visualization of structures that can be obscured by overlying or underlying tissue in a conventional mammogram.

To obtain images in mammography or tomosynthesis procedures, a patient's breast must first be compressed between a paddle and a stationary platform. This can be a very uncomfortable experience for most patients; one that is exacerbated, for example, when the system is imaging in the MLO orientation, where a significant amount of axilla tissue is squeezed between the paddle and platform. Pivoting paddles aim to increase comfort but may not necessarily achieve such results, since the paddle must be locked into a selected position prior to compression and furthermore may be constrained in at least 2 degrees of freedom. Additionally, freely rotating paddles may not provide sufficient compressive force.

SUMMARY

An exemplary compression system includes a breast compression paddle that is laterally movable, under manual control or when motorized and operating under software control. The compression paddle can shift automatically depending on the view to be acquired. For example, the paddle can be centered on the x-ray receptor for a CC view, shifted to one lateral side of the receptor for an MLO view of one breast and to the other lateral side of the receptor for an MLO view of the other breast. The paddle can be automatically recognized by the system when mounted so that the shifts can be adjusted to the type of paddle. Additionally or alternatively, the paddle is biased into a neutral position and can pivot in a number of orientations so as to decrease discomfort without detrimentally affecting compressive force. The compression paddle can be easily removable from a support that has a mechanism for laterally moving the paddle and for allowing the paddle to tilt for better conformance with the breast for selected image modes but locking the paddle against tilt for other modes.

This summary is provided to introduce a selection of concepts in a simplified form that are further described below in the Detailed Description. This summary is not intended to identify key features or essential features of the claimed subject matter, nor is it intended to be used to limit the scope of the claimed subject matter.

In one aspect, the technology relates to a system having: an imaging system housing; an x-ray source connected to the imaging system housing for delivering energy to a breast of a patient; a compression arm assembly housing connected to the imaging arm assembly; a support connected to the compression arm assembly housing, the support disposed between the x-ray source and the detector, wherein the source is configured to support the breast of the patient during delivery of the energy; a detector disposed in the support, such that a surface of the support is disposed between the x-ray source and the detector, the detector adapted to receive the delivered energy from the x-ray source; a paddle disposed between the support and the x-ray source, wherein a bottom surface of the paddle at least partially defines a plane, and wherein when in a rest position, the plane is substantially parallel to the support; and a pivot mechanism connecting the paddle to the compression arm assembly housing, wherein the pivot mechanism defines an axis of rotation substantially parallel to the sagittal plane of the patient, and wherein the pivot mechanism includes at least one biasing element for biasing the paddle into the rest position. In an embodiment, at least one biasing element has a pair of biasing elements. In another embodiment, at least one biasing element has a first pair of biasing elements and a second pair of biasing elements. In yet another embodiment, the first pair of biasing elements biases the paddle during a first range of rotation and the second pair of biasing elements biases the paddle during a second range of rotation. In still another embodiment, the first pair of biasing elements contacts the paddle during a first range of rotation and a second range of rotation, and one of the second pair of biasing elements contacts the paddle only during a second range of rotation.

In another embodiment of the above aspect, the pivot mechanism further defines an axis of rotation substantially parallel to the coronal plane of the patient. In an embodiment, at least one biasing element includes at least one of a constant-force biasing element and a variable-force biasing element. In another embodiment, the pivot mechanism is integral with the paddle. In yet another embodiment, the pivot mechanism is integral with the compression arm assembly housing and the paddle is removably connected to the pivot mechanism. In still another embodiment, the system further includes a sensor for detecting a position of the paddle relative to the pivot mechanism.

In another aspect, the technology relates to an apparatus having: a paddle for compressing a breast during a breast imaging procedure; a bracket pivotably connected to the paddle, wherein the bracket is adapted to be removably connected to an imaging system; and at least one biasing element disposed between the bracket for biasing the paddle into a substantially neutral position about an axis of rotation substantially parallel to the sagittal plane. In an embodiment, the bracket includes a plurality of co-axial axles, and the paddle defines a plurality of openings, wherein each of the plurality of openings is adapted to receive one of the plurality of axles. In another embodiment, the apparatus further includes a lock for selectively preventing pivoting of the paddle relative to the bracket. In yet another embodiment, the paddle has two side edge surfaces and a central surface, wherein the two side edge surfaces define a plane and the central surface is disposed on one side of the plane. In still another embodiment, the paddle further includes a front wall and a rear wall disposed proximate the bracket, wherein the central surface extends from the front surface to the rear wall, and wherein the front wall is disposed farther from the plane than the rear wall.

In another embodiment of the above aspect, the paddle has a substantially concave bottom surface. In an embodiment, at least one biasing element includes a pair of biasing elements. In another embodiment, the at least one biasing element has a first pair of biasing elements and a second pair of biasing elements. In yet another embodiment, the first pair of biasing elements biases the paddle during a first range of rotation and a second range of rotation and the second pair of biasing elements biases the paddle only during the second range of motion. In still another embodiment, the at least one biasing element includes at least one of a constant-force biasing element and a variable-force biasing element.

BRIEF DESCRIPTION OF THE DRAWINGS

The same number represents the same element or same type of element in all drawings.

DETAILED DESCRIPTION

Figure 1:
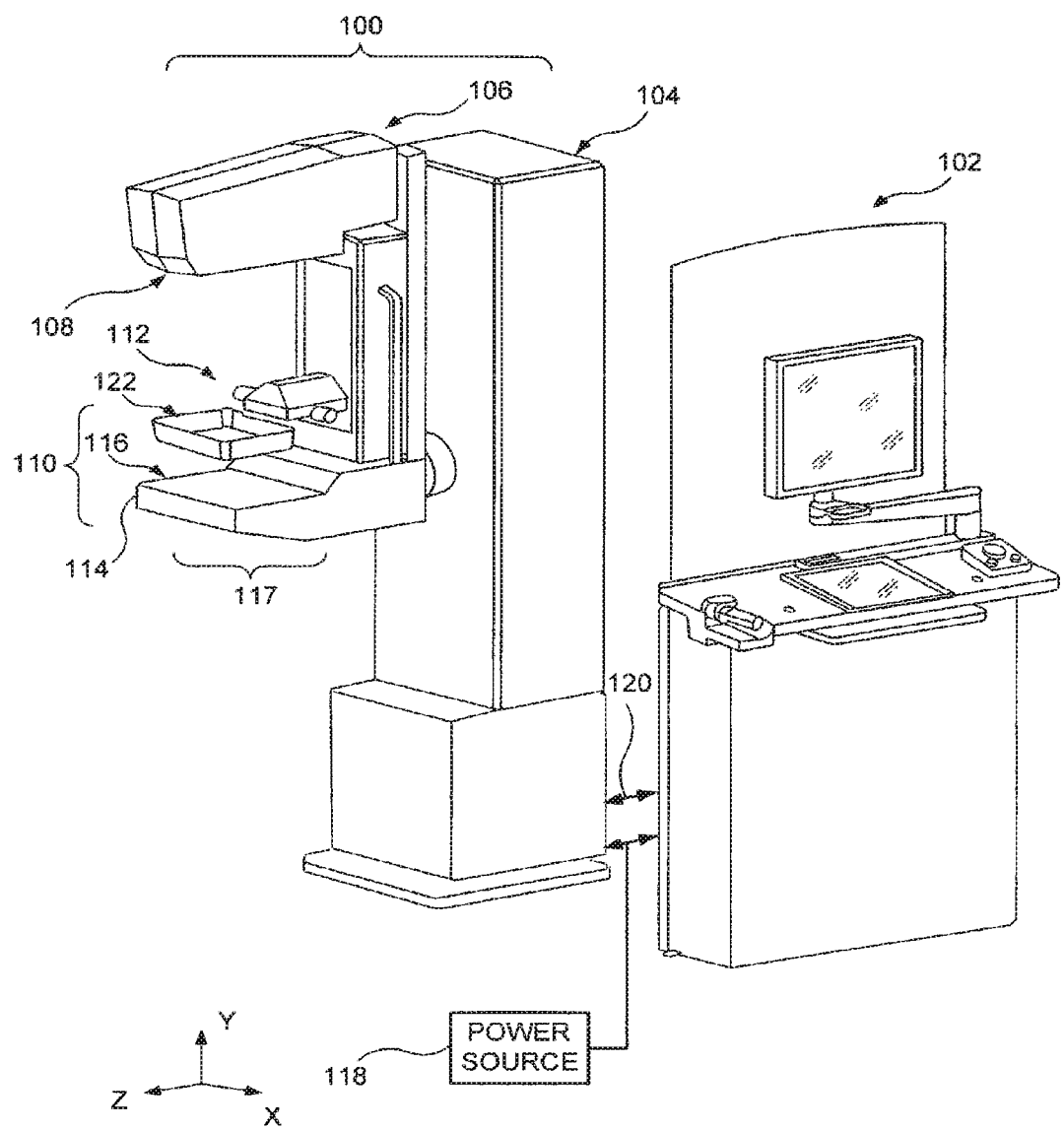
FIG. 1 is a perspective view of a gantry and an acquisition workstation in accordance with an example of the disclosed system.

In describing examples and preferred embodiments illustrated in the drawings, specific terminology is employed for the sake of clarity. However, the disclosure of this patent specification is not intended to be limited to the specific terminology so selected and it is to be understood that each specific element includes all technical equivalents that operate in a similar manner.

FIGS. 1-5 illustrate a non-limiting example of a multimode mammography/tomosynthesis system comprising a gantry 100 and a data acquisition work-station 102. Gantry 100 includes an imaging arm assembly 104 supporting a tube arm assembly 106 rotatably mounted thereon to pivot about a horizontal axis 402 (FIG. 4) and carrying an x-ray tube assembly 108. X-ray tube assembly 108 includes (1) an x-ray tube generating x-ray energy in a selected range, such as 20-50 kV, at mAs such as in the range 3-400 mAs, with focal spots such as a nominal size 0.3 mm large spot and nominal size 0.1 mm small spot (2) supports for multiple filters such as molybdenum, rhodium, aluminum, copper, and tin filters, and (3) an adjustable collimation assembly selectively collimating the x-ray beam from the focal spot in a range such as from 7×8 cm to 24×29 when measured at the image plane of an x-ray image receptor included in the system, at a maximum source-image distance such as 75 cm. Also mounted on housing 104, for rotation about the same axis 402, is a compression arm assembly 110 that comprises a compression plate 122 and a receptor housing 114 having an upper surface 116 serving as a breast plate and enclosing a detector subsystem system 117 comprising a flat panel x-ray receptor 502 (FIG. 5), a retractable or decouplable anti-scatter grid 504 and, optionally, a mechanism 506 for driving and retracting anti-scatter grid 504. Housing 104 also encloses the following components schematically illustrated in FIG. 4: a vertical travel assembly 404 for moving tube arm assembly 106 and compression arm assembly 110 up and down to accommodate a particular patient or imaging position, a tube arm assembly rotation mechanism 406 to rotate tube arm assembly 106 about axis 402 for different imaging positions, a detector subsystem rotation mechanism 408 for rotating components of detector subsystem 117 (such as x-ray receptor 502) about axis 402 to accommodate different operations modes, and couple/uncouple mechanism 410 to selectively couple or uncouple tube arm assembly 106 and compression arm assembly 110 to and from each other, and tube arm assembly 106 and detector subsystem 117 to and from each other. Housing 104 also encloses suitable motors and electrical and mechanical components and connections to implement the functions discussed here. A patient shield 200, schematically illustrated in FIG. 2, can be secured to compression arm assembly 110 to provide a mechanical interlock against patient contact with the rotating x-ray tube arm assembly 106. Work-station 102 comprises components similar to those in the Selenia® or Selenia® Dimensions® mammography system, including a display screen (typically a flat panel display that may include touch-screen functionality), user interface devices such as a keyboard, possibly a touch-screen, and a mouse or trackball, and various switches and indicator lights and/or displays. Work-station 102 also includes computer facilities similar to those of the Selenia® system (but adapted through hardware, firmware and software differences) for controlling gantry 100 and for processing, storing and displaying data received from gantry 100. A power generation facility for x-ray tube assembly 108 may be included in housing 104 or in work-station 102. A power source 118 powers work-station 102. Gantry 100 and work-station 102 exchange data and controls over a schematically illustrated connection 120.

Figure 6:
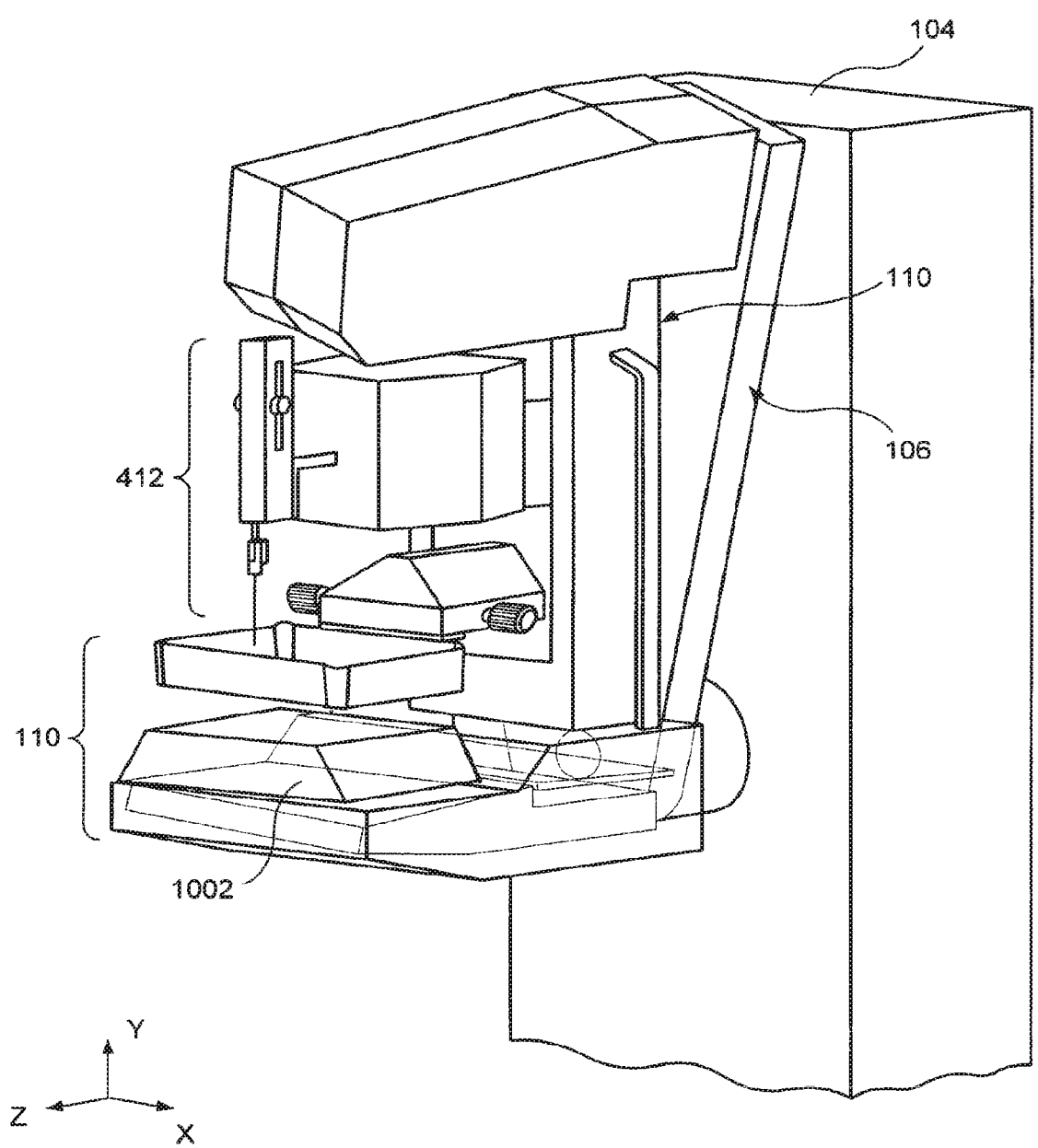
FIG. 6 is a perspective view of the structure of FIG. 4.

In standard mammography mode, typically used for screening mammography, tube arm assembly 106 and compression arm assembly 110 are coupled and locked together by 410 in a relative position such as seen in FIG. 1, such that an x-ray beam from x-ray tube assembly 108 illuminates x-ray receptor 502 when the patient's breast is compressed by compression device 112. In this mode, the system operates in a manner similar to said Selenia® system to take a mammogram. Vertical travel assembly 404 and tube arm rotation mechanism 406 can make vertical adjustments to accommodate a patient, and can rotate tube arm assembly 106 and compression arm assembly 110 together as a unit about axis 402 for different image orientations such as for CC and for MLO images. For example, tube arm assembly 106 and compression arm assembly 110 can rotate (between) (−195°) and (+150° about axis 402. As in the Selenia® system, compression device 112 includes a compression paddle 122 that can move laterally, in a direction along the chest wall of a patient, to adjust for different imaging orientations. However, as described further below, the mechanism for supporting and moving compression paddle 122 is different. Typically, anti-scatter grid 504 is over x-ray receptor 502 in the standard mammography mode to reduce the effect of x-ray scatter. FIG. 6 illustrates an example of the operation of detector subsystem 117 in standard mammography. Of course, these are only examples; other workflow steps or orders of steps can be used instead.

In a diagnostic mode, the patient's breast can be spaced from upper surface 116, for example by an x-ray translucent spacer gantry 1002 (FIG. 6), with the system otherwise similar to FIG. 1, for a magnification of up to 1.8, for example. In this mode, as in standard mammography, tube arm assembly 106 and compression arm assembly 110 are locked to each other and can move up or down and rotate about axis 402 for different image orientation. A different spacer 1002 can be used for a different degree of magnification. Also, differently shaped or dimensioned compression paddles 122 can be used for different breast compression effects. The x-ray tube in x-ray tube assembly 108 can be set to a smaller focal spot size to improve a diagnostic image. In this mode, anti-scatter grid 504 typically is retracted when magnification is used such that grid 504 is completely out of the image. The user can elect not to use a spacer 1002 in diagnostic imaging, in which case anti-scatter grid 504 can be used over the entire image.

In a dynamic imaging mode, a number of breast images are taken while the patient's breast remains compressed. In one technique, an agent such as iodine is injected into the patient and after a suitable waiting time such as about one minute for a maximum uptake, two images breast are taken in rapid succession, for example one at an x-ray energy just above the K-edge of iodine and one at an energy just below the K-edge. Alternatively, a succession of breast images can be taken at a single x-ray energy band or bands just above and below the K-edge, or at another x-ray energy range, to track the uptake of agent over time. Another technique adds taking a baseline breast image before or soon after injecting the agent and using it together with later breast images to generate subtraction images that provide better visualization of anatomy that may be of interest. Still another dynamic imaging mode technique comprises injecting a contrast agent and taking a succession of images over a period such as 5-7 minutes, for example one image every minute, and processing the image data to generate for each pixel, or at least for each pixel of interest, a histogram of the change in the pixel value, to thereby use the manner in which pixel values change to differential abnormal tissue. For this mode, work-station 102 can store preset data that commands gantry 100 and work-station 102 to take a desired sequence of images for the dynamic mode technique selected by the operator, such that the command data sets the appropriate parameters such as x-ray energy, dose, timing of images, etc. Alternatively, such processing to assess changes in pixel values can be done for a region of interest rather than over individual pixels, to produce information such as a measure of changes in the average pixel values in the region of interest.

Figure 2:
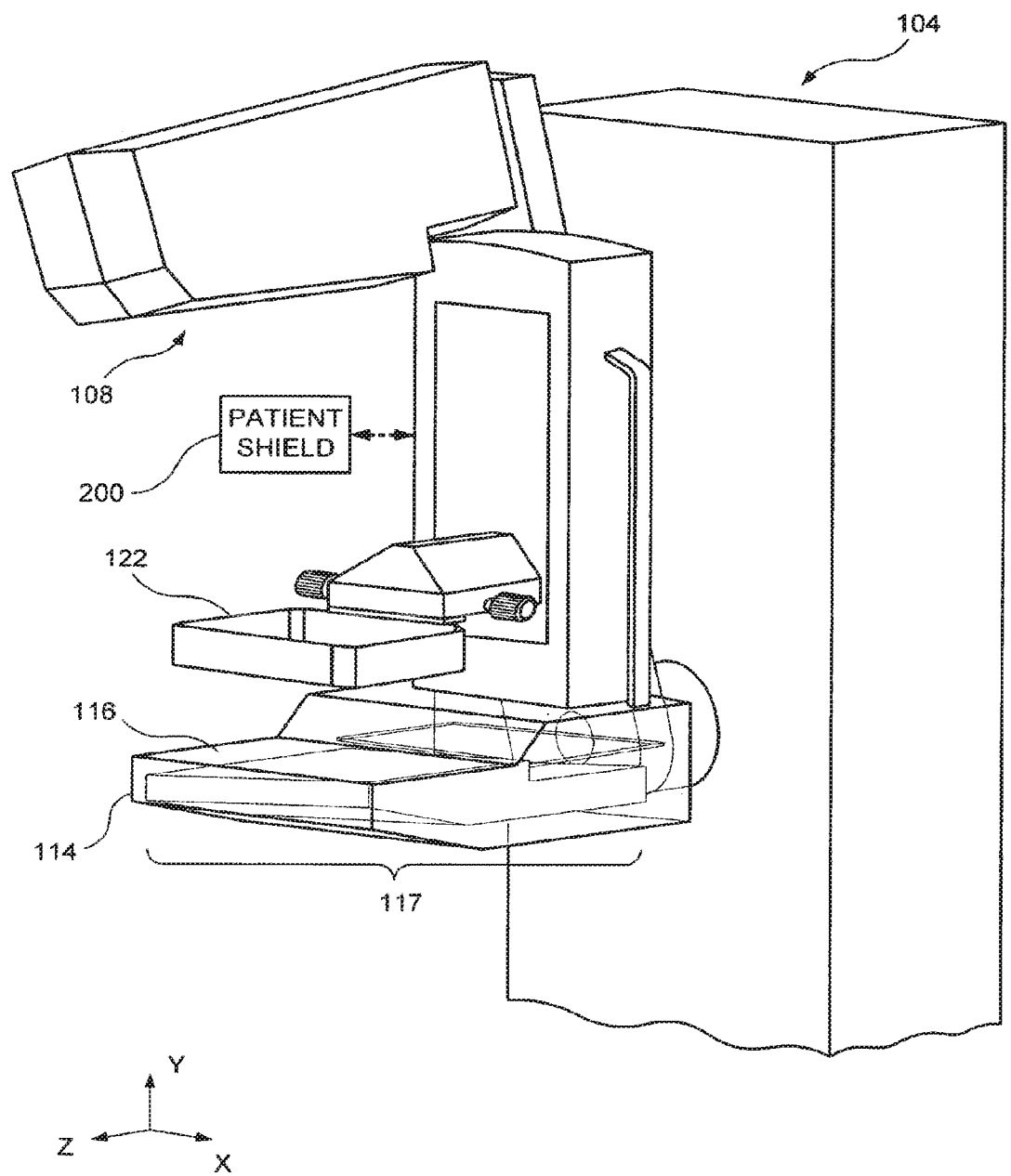
FIG. 2 is an enlarged view of a portion of the system of FIG. 1, with a tube arm assembly in a rotated position.
Figure 3:
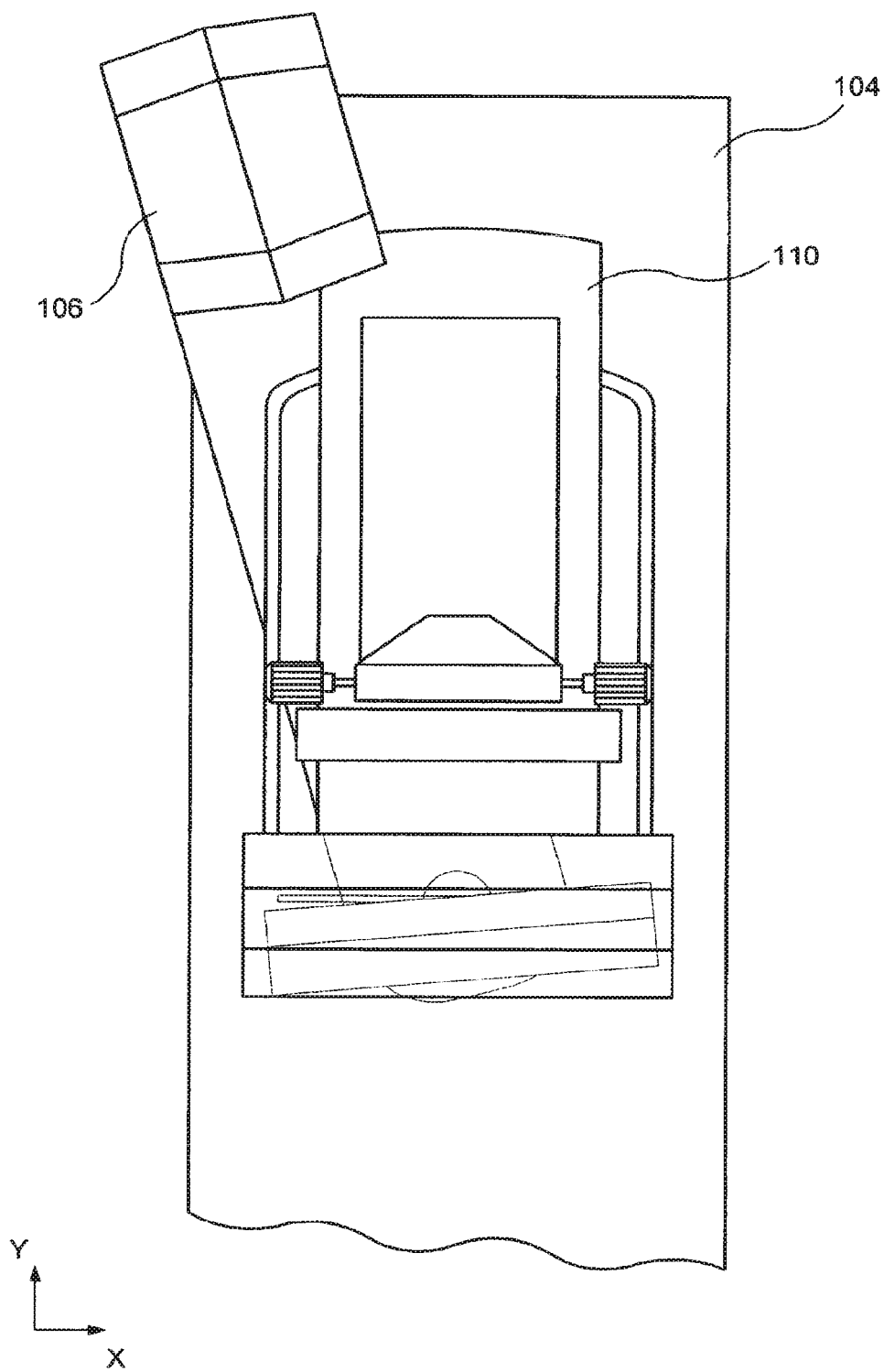
FIG. 3 is a front elevation of the apparatus of FIG. 2.
Figure 4:
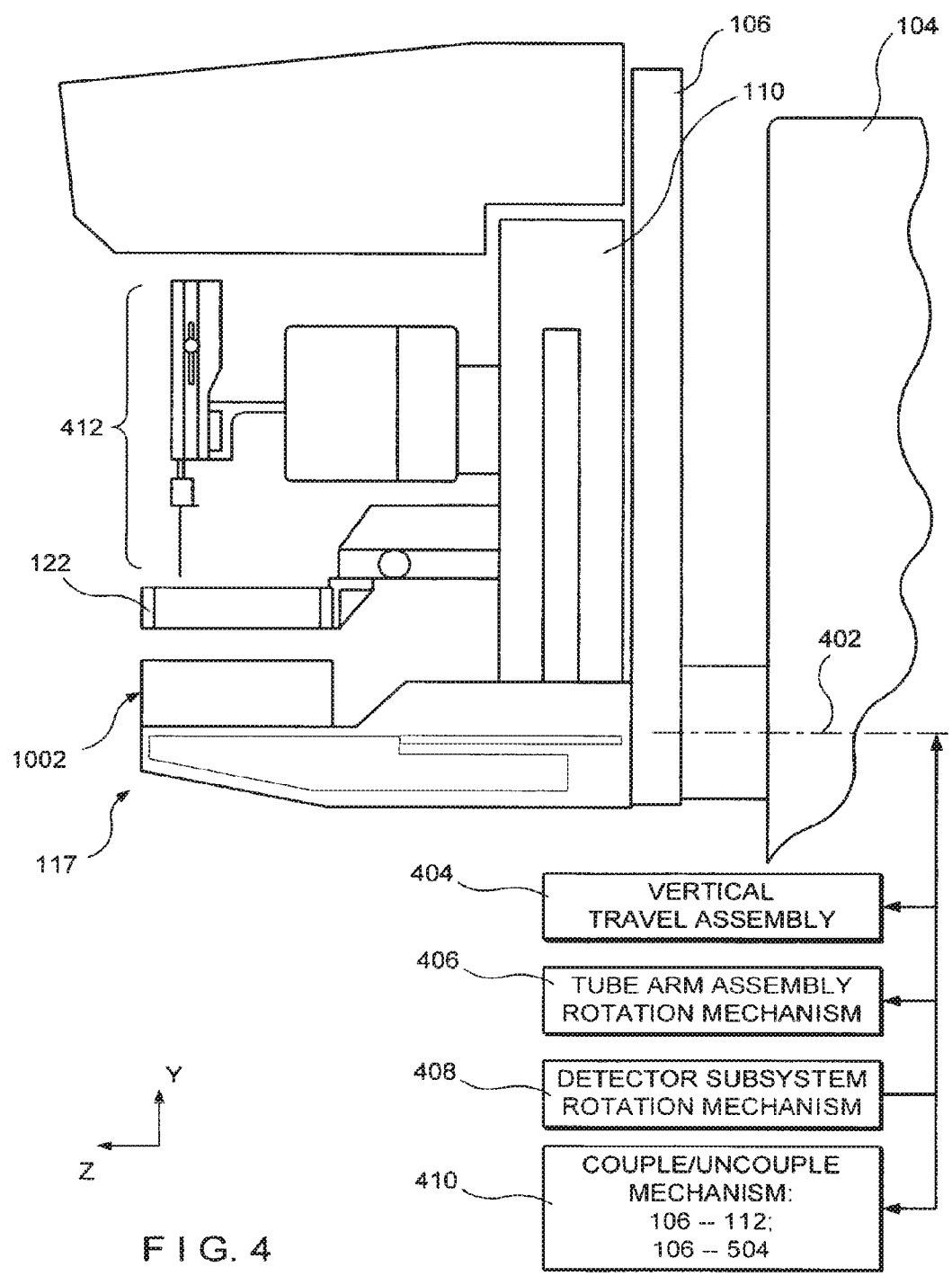
FIG. 4 is a side view of a gantry with a biopsy station and a spacer, with schematic illustration of other mechanisms.
Figure 7:
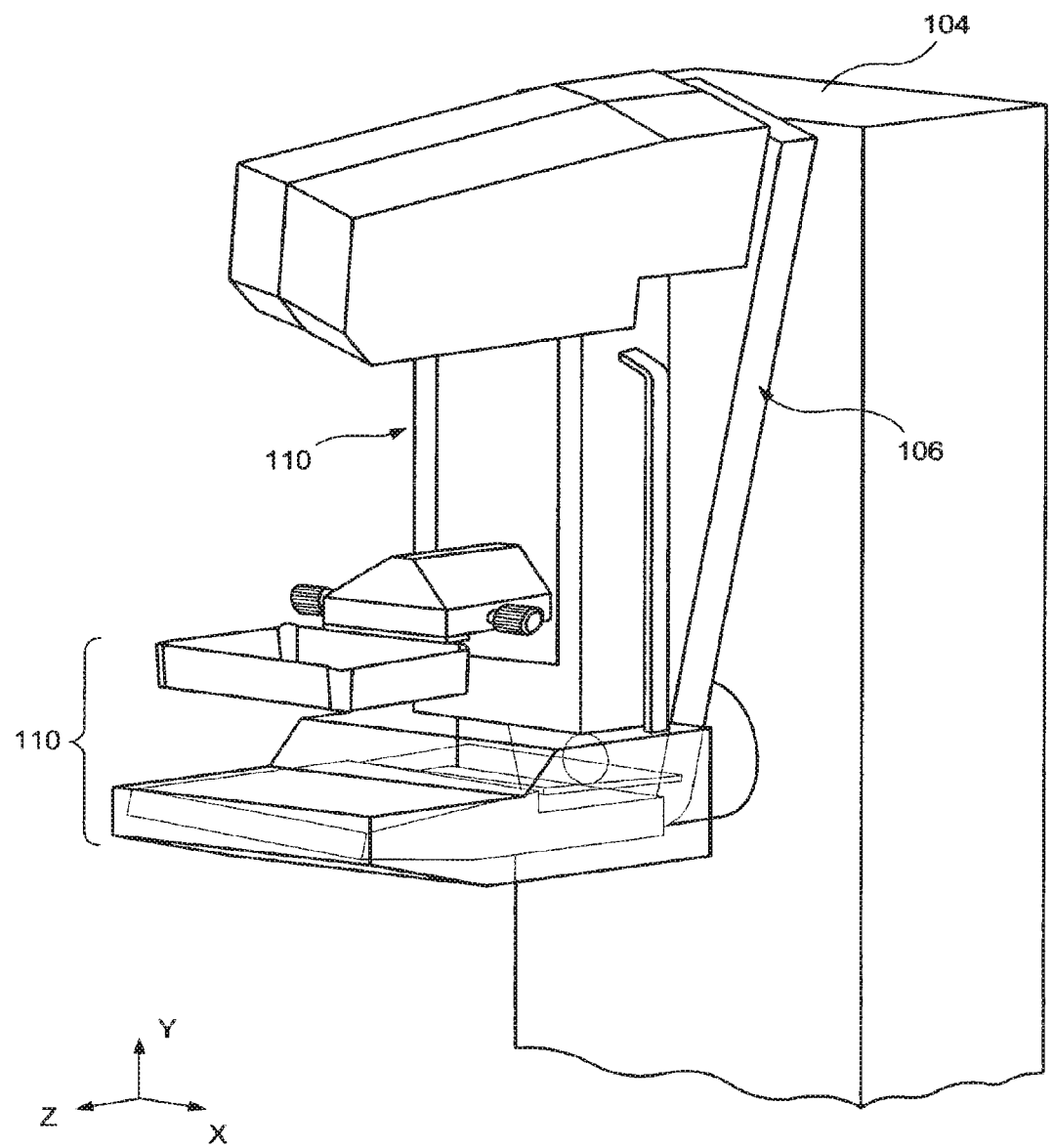
FIG. 7 is similar to FIG. 2 but shows a tube arm assembly angled differently.
Figure 8:
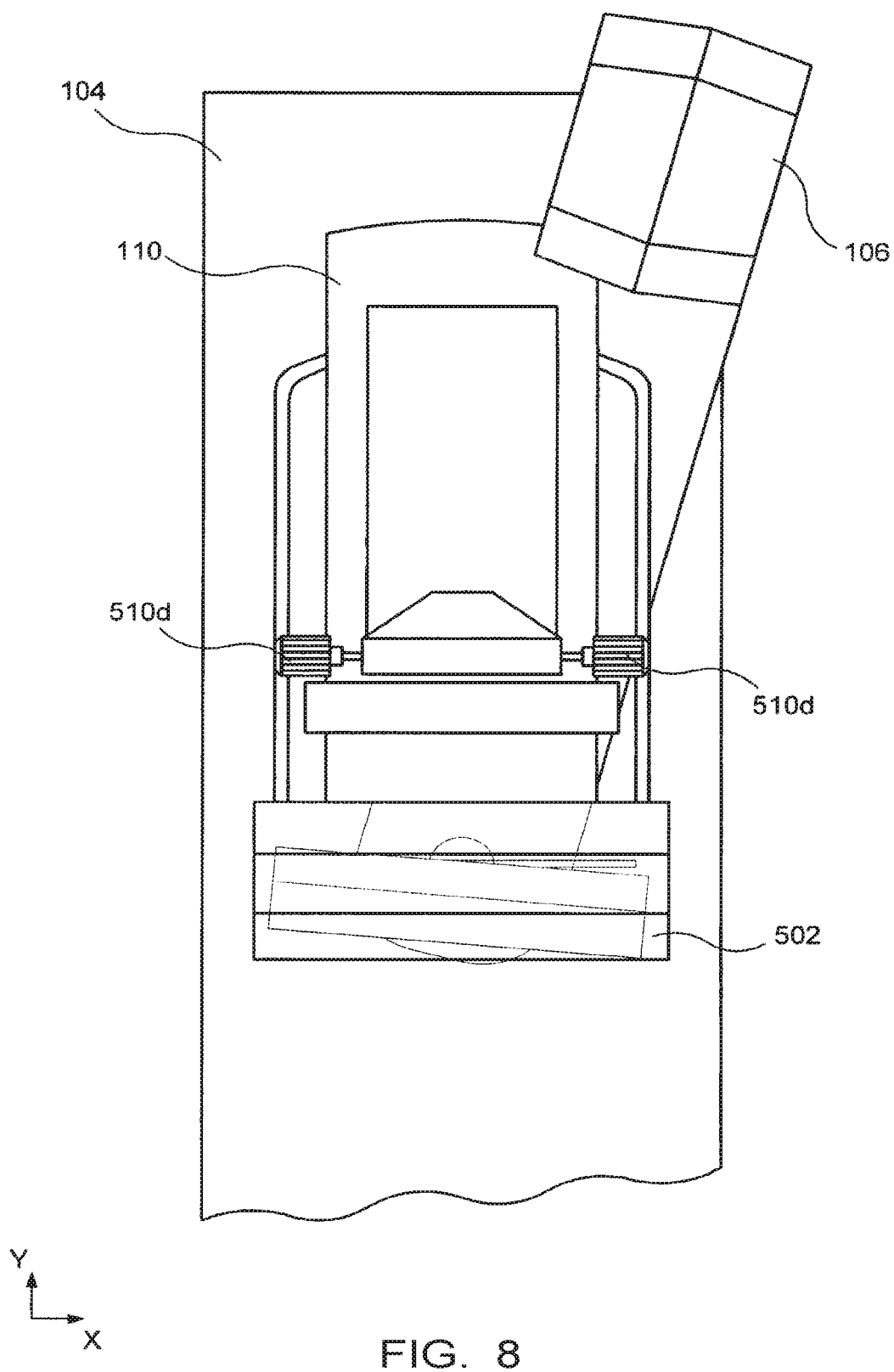
FIG. 8 is a front elevation of the structure of FIG. 7.

In tomosynthesis mode, tube arm assembly 106 and compression arm assembly 110 are decoupled by unit 410 such that compression arm assembly 110 stays in one position, compressing the patient's breast, while tube arm assembly 106 rotates about axis 402, for example between the position illustrated in FIG. 2 to that illustrated in FIG. 7, or ±15° relative to compression arm assembly 110. Tomosynthesis can be carried out for different image orientations, so that compression arm assembly 110 can be rotated about axis 402 (alone or together with assembly 106) for a desired image orientation and locked in place, and then tube arm assembly 106 can be rotated relative to that position of compression arm assembly 110 for tomosynthesis imaging over ±15° or some other desired angular range. In one example, 11 images are taken during an angular sweep of tube arm assembly 106, one every approximately 3°. However, a different number of images can be taken, for example up to 21 during a single sweep. For tomosynthesis images, the x-ray tube in x-ray tube assembly 108 continuously rotates and the x-ray tube is pulsed for each image, for example, for x-ray energy pulses each lasting approximately 100 mSec, although pulses of different duration can be selected. Alternatively, the rotational motion can stop for taking each image, or continuous motion without pulsing can be used (and the timing of data measurements relied to define pixel values). As seen in FIGS. 2, 3, 5, 7 and 8, in this mode mechanism 506 fully retracts anti-scatter grid 504 away from x-ray receptor 502 so grid 504 is out of the image. Also as seen in these figures, while the breast remains immobilized in compression arm assembly 110 during the angular sweep of tube arm assembly 106, x-ray receptor 502 rocks within receptor housing 114. In this rocking motion, controlled by unit 408 (FIG. 4), a line normal to the image face of x-ray receptor 502 may keep pointing to the focal spot of the x-ray tube in x-ray tube assembly 108. Alternatively, the rotation of tube arm assembly 106 and rocking of x-ray receptor 502 can be through different angles; for example, tube arm assembly 106 can rotate through 15° while x-ray receptor 502 rocks through 5°, i.e. the rocking angle can be an amount one-third that of assembly 108. Synchronous rotation of tube arm assembly 106 and rocking of x-ray receptor 502 can be achieved by controlling separate motors for each or, alternatively, through using a motor to drive tube arm assembly 106 and a mechanical coupling between the rotation of tube arm assembly 106 and rocking of x-ray receptor 502. Image data can be obtained and processed into tomosynthesis images for display and/or storage as described in U.S. Patent Publication No. 2005/0113681, the disclosure of which is hereby incorporated by reference in its entirety. Again, these are only examples, and other steps or orders of steps can be used instead.

In a combination mode, during a single compression of the patient's breast the system takes a conventional Mammogram and tomosynthesis images. In this mode, while the breast remains compressed in compression arm assembly 110, (1) tube arm assembly 106 sweeps and x-ray receptor 502 rocks, each through an appropriate angle, and exposures are taken for tomosynthesis images, and (2) a standard mammogram is taken. The standard mammogram can be taken at a 0° relative angle between tube arm assembly 106 and a normal to the imaging plane of x-ray receptor 502, and can be taken before or after the tomosynthesis images are taken or between the taking of two successive tomosynthesis images. Typically, each tomosynthesis image utilizes substantially lower x-ray dose than the standard mammogram. For example, the total x-ray dosage for tomosynthesis imaging in one sweep of tube arm assembly 106 can be approximately the same as that for a single standard mammogram, or up to approximately three times that dosage. The relationship between the two dosages can be user-selected. Again, these are examples, and different steps or orders of steps can be used instead. For example, a preferred approach may be to take the standard mammogram first, then move arm 106 to one end of its rotational range for tomosynthesis and take the tomosynthesis images. The order in which the two types of images are taken may be optimized such that the overall imaging time is minimized, and an order that achieves such minimization can be the preferred order. The exposure (tube current mA, tube voltage kVp, and exposure length msec) techniques for the standard mammogram and the tomosynthesis exposures can be set manually, or by using automatic methods. If the standard mammogram is taken first, its exposure techniques can be used to set an optimal technique for the subsequent tomosynthesis images, and vice versa. The exposure technique can be modified dynamically, if the software senses that the signal reaching the image receptor is either too low or too high and adjust subsequent exposures as needed.

In a stereotactic mode, during a single compression of the patient's breast at least two images of taken, for example one at (+15°) angle and one at (−15° angle of tube arm assembly 106 relative to compression arm assembly 110, although other angles can be used and more images can be taken. X-ray receptor 502 can remain in place for this procedure, or can be rocked through a selected angle, for example through an angle sufficient to maintain the same orientation of the imaging surface of receptor 502 relative to tube arm assembly 106. A spacer 1002 can be used for magnification. If x-ray receptor 502 remains in place despite rotation of arm 106, or if spacer 1002 is used, anti-scatter grid 504 is fully retracted; if x-ray receptor 502 maintains its orientation relative to tube arm assembly 106 and not spacer 1002 is used, anti-scatter grid 504 need not be retracted. As is known in the art, the two or more images can be used to identify the location of a lesion, so that needle biopsy can be used, for example with an upright needle biopsy station 412 (FIG. 4) in a manner similar to that used with the commercially available Selenia™ system and StereoLoc II™. A compression paddle 122 appropriate for needle biopsy typically is used when taking the stereotactic images. Alternatively, some or all of the images taken in the tomosynthesis mode and/or in the combined mode can be used to identify the location of a lesion for biopsy, in which case a compression paddle 122 appropriate for the purpose typically is used when taking the images.

In needle localization mode, x-ray images can be taken after a biopsy or other needle is inserted into the compressed breast. For this purpose, imaging such as in the stereotactic mode, the tomosynthesis mode, or the combined mode can be used.

In the disclosed system, compression paddle 122 is movable laterally, as generally described in U.S. Patent Application Publication No. 2005/0063509, the disclosure of which is hereby incorporated by reference herein in its entirety. In addition, compression paddle 122 can pivot about an axis along the patient's chest wall to conform the breast shape in certain procedures, as discussed in said U.S. Pat. No. 5,706,327, the disclosure of which is hereby incorporated by reference herein in its entirety. Other configurations for enabling pivoting movement of the compression paddle 122 about various axes are described herein.

Figure 5:
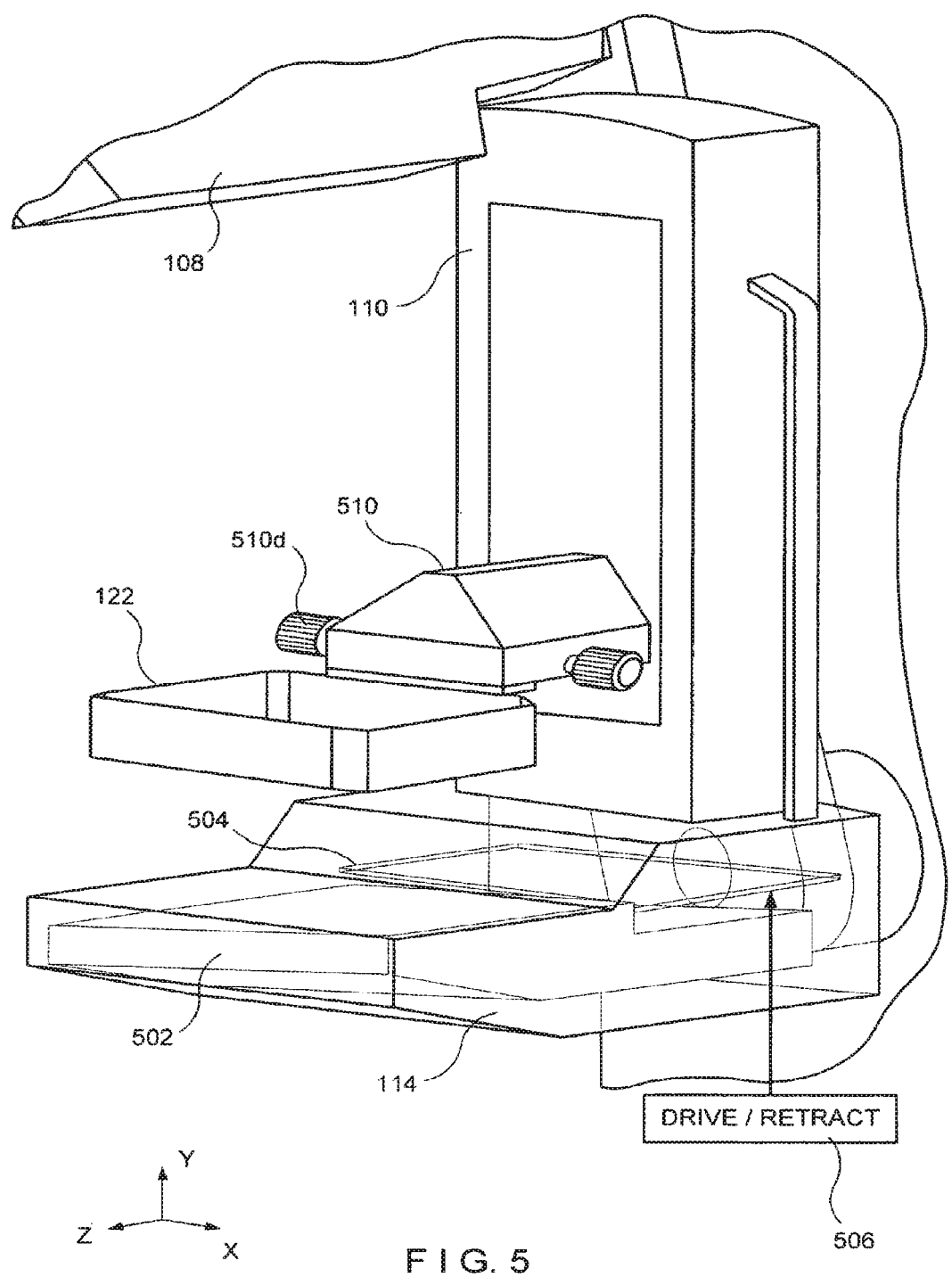
FIG. 5 is an enlarged view of a portion of FIG. 1.
Figure 9:
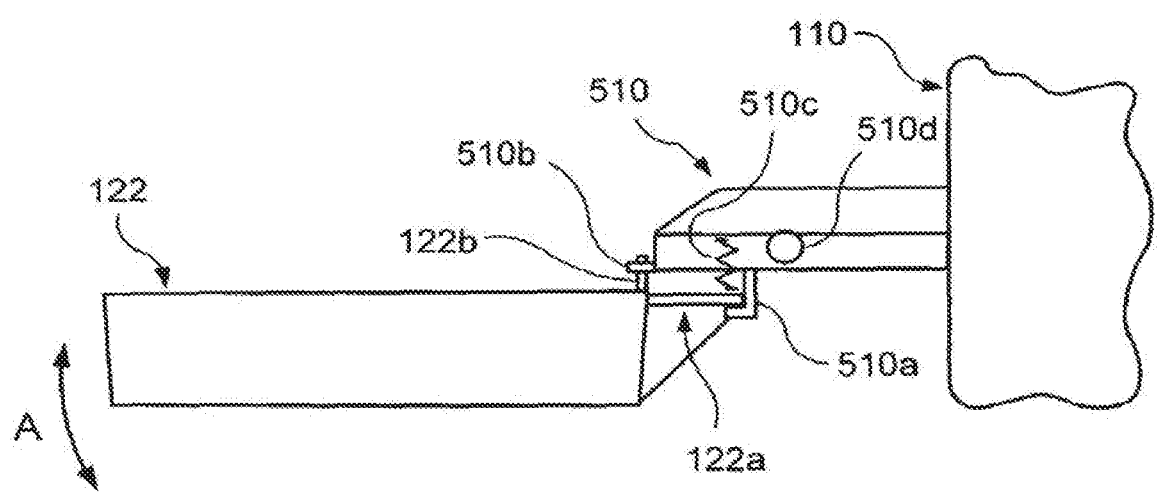
FIG. 9 is an enlarged side view of a structure for removably mounting a breast compression paddle.

As illustrated in FIGS. 5 and 9, compression paddle 122 is removably mounted to a support 510 that moves up and down compression arm assembly 110 as needed for breast compression. To mount compression paddle 122 onto 510, a projection compression paddle 122a of the paddle engages a projection 510a of the support, and a projection 122b of the paddle latches onto projection 510b of the support. Projection 510a is spring-loaded, such as by a spring schematically illustrates at 510c to allow for pivoting compression paddle 122 about an axis where it latches onto 510, as illustrated by arrow A, for better conformance with the compressed breast in some imaging protocols. Other imaging protocols may require compression paddle 122 not to pivot, in which case projection 510a is locked in place by a locking mechanism in 510 (not shown) to keep compression paddle 122 in place relative to support 510. The locking mechanism can be manually set to a lock position, and manually unlocked by the operator. Alternatively, the locking mechanism can be controlled through an operator input at gantry 100 or workstation 102. A sensing mechanism can be included to sense whether compression paddle 122 is locked against pivoting, to provide information that work-station 102 can use for setting imaging protocols such as for automated breast compression and automated exposure methods. Two knobs 510d, one on each lateral side of support 510, can be manually rotated to move projection 510b and thus compression paddle 122 laterally such that it compress a breast that is not centered laterally on upper surface 116, for example for MLO imaging. Each knob 510d can operate a mechanism such as an endless screw rotating in a nut secured to projection 510b. Alternatively, or in addition, projection 510b and thus compression paddle 122 can be driven laterally by a motor, under control of operator switches or other interface at gantry 100 or at work-station 102, or automatically positioned laterally under computer control.

Importantly, compression paddle 122 is driven for lateral movement by components that are a part of support 510. Thus, compression paddle 122 can be simple structure, and can even be disposable, with a new one used for each patient or for only a few patients. This can simplify and reduce the cost of using the system, because an imaging facility usually stocks a number of different paddles for different purposes. If the lateral movement mechanism is integral with a compression paddle, the paddle assembly is considerably larger, heavier and more expensive. But with a compression paddle 122 that relies for lateral movement on support 510, and is easily mounted by hand and without tools to support 510, by sliding compression paddle 122a into projection 510a and latching projection paddle 122b onto projection 510b, and is easily removed by reversing the process, the expense of keeping a number of different compression paddles in stock or replacing paddles with new ones is greatly reduced, as are the time and convenience when changing from one type of compression paddle to another. Compression paddle 122 can include a bar code that is automatically read by a bar code reader in support 510, to keep work-station 102 informed of the paddle currently mounted to support 510, for use in automating imaging protocols. For example, the bar code information can be checked to ensure through computer processing that the type of paddle that is currently mounted on support 510 matches the imaging that will be commanded, and the information from the sensor for whether compression paddle 122 is locked in non-tilting mode can be used to automatically make adjustments for compression height to ensure accurate automatic x-ray exposure operation. Further, the bar code information identifying the paddle can be used to automatically set collimation in x-ray tube assembly 108 so that the x-ray beam matches the size and shape of the currently installed compression paddle 122.

Figure 10A:
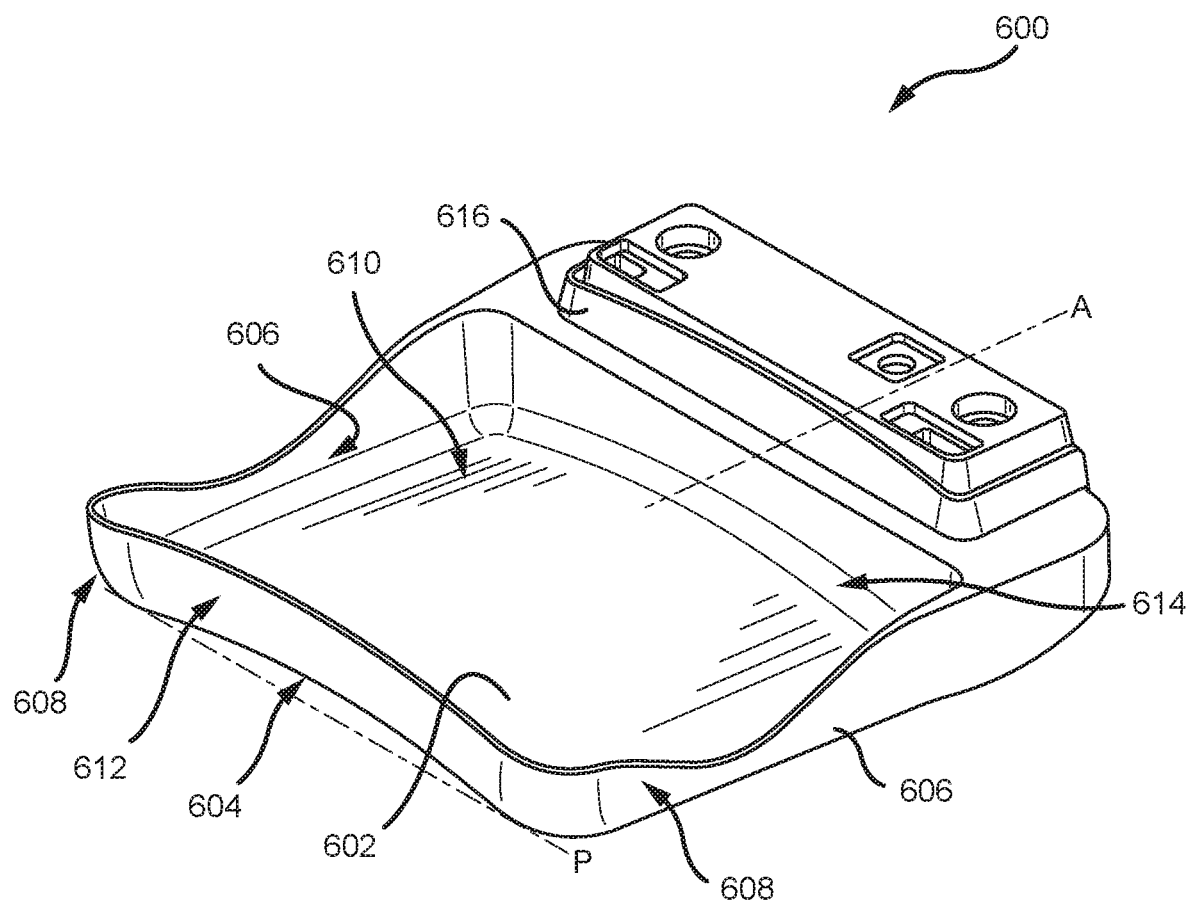
FIG. 10A is a perspective view of a breast compression paddle.
Figure 10B:
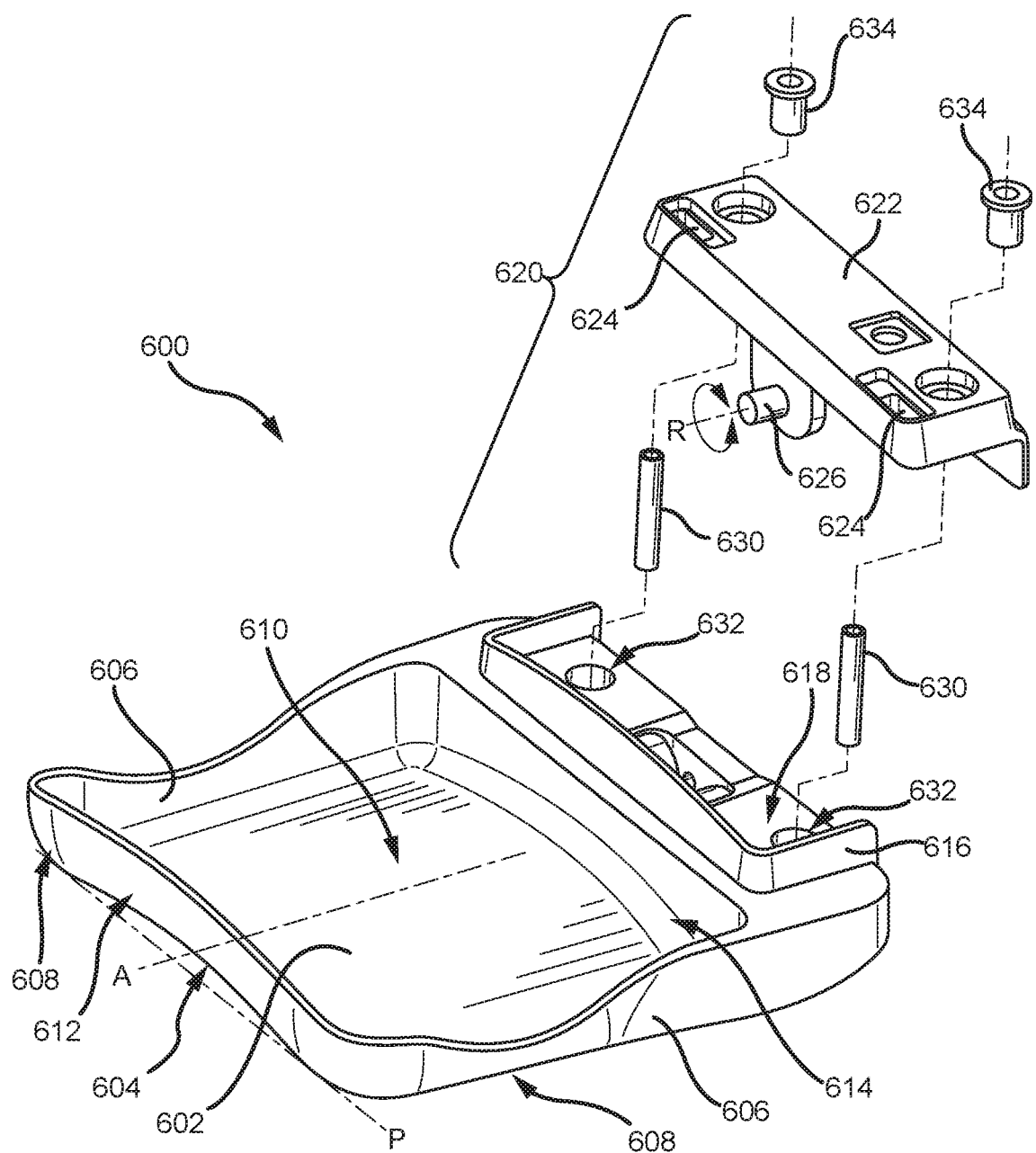
FIGS. 10B and 10C are exploded perspective views of the breast compression paddle of FIG. 10A.
Figure 10C:
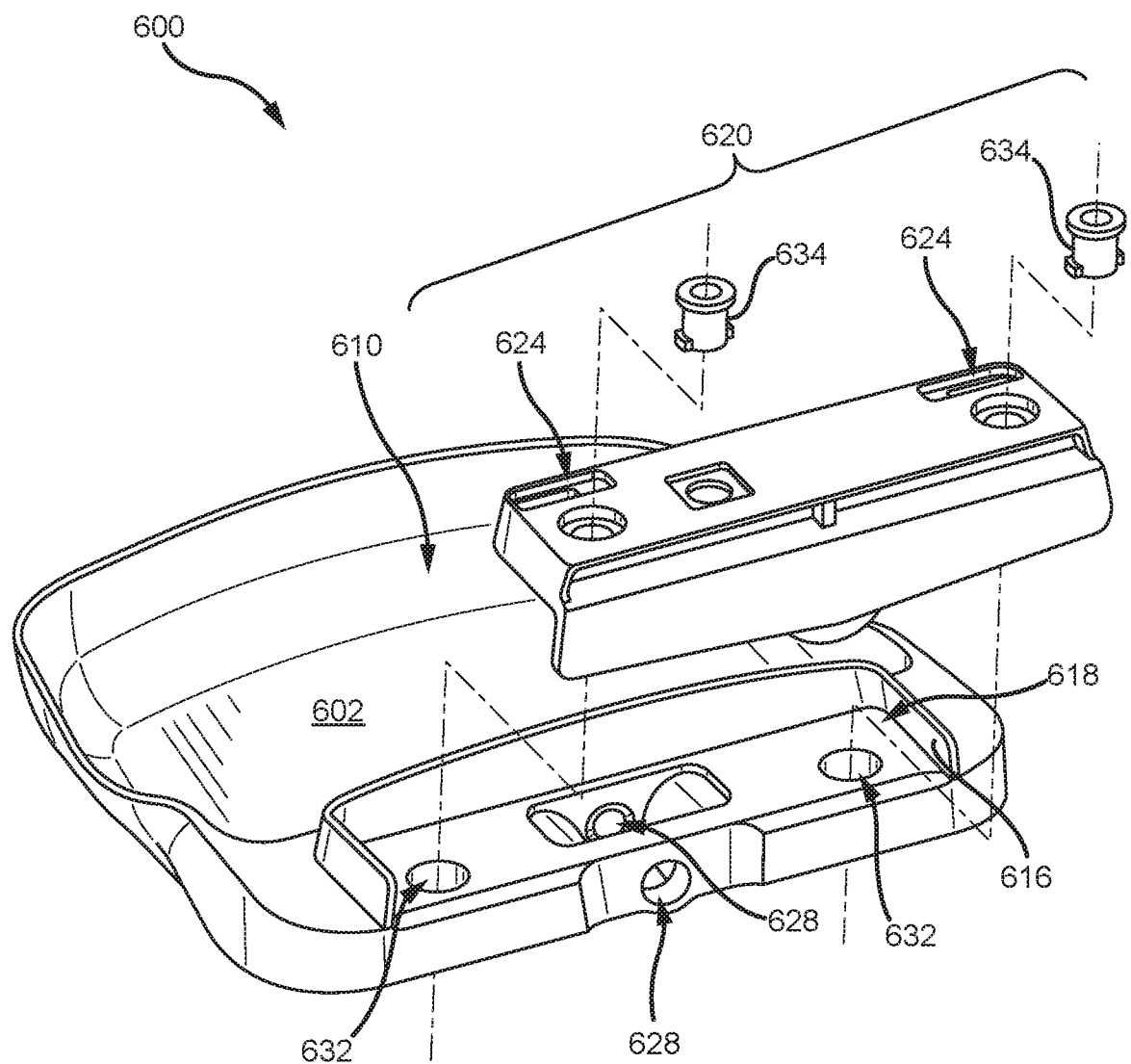

FIG. 10A is a perspective view of a breast compression paddle 600. FIGS. 10B and 10C are exploded perspective views of the breast compression paddle 600 of FIG. 10A. FIGS. 10A-10C are described simultaneously. The paddle 600 includes a wall 602 that includes a generally concave surface 604, which may correspond in shape to a breast and/or a compressed breast. The wall 602 may define a window (not shown) so as to allow the paddle 600 to be used in biopsy procedures. The generally concave surface 604 can extend between the side walls 606 of the compression paddle 600. The generally concave surface 604 helps to distribute more equally forces applied to the breast so as to more closely correspond to the shape of the breast. Such a configuration may help provide more comfort to a patient as the breast is being compressed. The generally concave surface 604 includes two outer edge portions 608 that define a reference plane P, as well as a central portion 610. The central portion 610 is non-coplanar with the outer edge portions 608, such that the central portion 610 is raised relative to or disposed above the reference plane P. The central portion 610 may be level along its length (e.g., parallel to the reference plane P or an axis A of the paddle 600) or may be pitched downward from a front wall 612 to a rear wall 614 of the paddle 600. This may help further conform the paddle 600 to the shape of the breast.

The generally concave surface 604 may also help to prevent the breast from slipping and moving during image acquisition. As an example, this configuration may help prevent slipping of the breast in the MLO position by supporting the breast more, in comparison to known flat compression paddles that often allow the breast to slip during image acquisition. The generally concave surface 604 may have smooth curvature or can have any other shape that is generally concave, e.g., the surface 604 may include ridges, lines, and/or other elements from injection molding the compression paddle 600, the surface 604 may have a generally trapezoidal shape, etc. Additionally or alternatively, the compression paddle 600 can be used to compress a patient's breast with or without an inflatable jacket and/or a gel pad. In another embodiment, the generally concave surface 604 may not be uniformly concave from the front wall 612 (i.e., the chest facing wall) to the rear wall 614. As compressed breast tissue may not extend as far back as the rear wall 614, the concavity may be greater near the front wall 612 compared to the rear wall 614. As an example, the bottom surface 604 may be generally concave near the front wall 612 and may be flatter near the rear wall 614. In an additional or alternative example, the radius of the generally concave surface 604 is greater near the front wall 612 compared to the bottom surface 604 near the rear wall 614. This non-uniformity may help to provide more even compression from the nipple to the chest wall of the breast.

Generally, the compression paddles of the present technology described herein may be more comfortable to a patient undergoing breast compression during a mammogram or x-ray imaging of the breast. The compression paddles of the present technology described herein generally require less compression force to be applied to some or all areas of the breast to accomplish the same tautness as that of a known flat compression paddle. The paddles may be manufactured of substantially rigid or flexible materials. Use of rigid materials allows the paddle to sufficiently compress the breast without deforming. For example, in the embodiment depicted in FIGS. 10A-10C, a distance between the central portion 610 and the reference plane P may be substantially the same when the paddle 600 is compressing a breast or not compressing a breast. For example, the concave contour of the wall 602 may be substantially the same. The particular shapes and contours of disclosed herein may reduce or eliminate discomfort during breast compression.

A collar 616 at least partially defines a receiver 618 for receiving a pivot mechanism 620. The pivot mechanism 620 includes a pivot bracket 622 that defines a plurality of openings 624. The openings 624 are configured to receive one or more mounting brackets that extend from the support on the compression arm assembly, as depicted above. These mounting brackets may be configured to pivot as depicted in FIG. 9 or as otherwise known in the art. Thus, the bracket 622 is supported by the compression arm assembly and the paddle 600 is able to pivot as described below. The bracket 622 includes, in the depicted embodiment, a plurality of axles 626. These axles 626 are configured to be aligned with and received in one of the plurality of openings 628 defined by the paddle 600, thus allowing for pivotal movement of the paddle 600. In general, the axles 626 define an axis of rotation R that is substantially parallel to the sagittal plane. One or more biasing elements 630 may be received in wells 632 defined by the paddle 600. In the depicted embodiment, the wells 632 are disposed within the receiver 618. Caps 634 close the wells 632 and may be rotated so as to adjust the compression of the biasing elements 630. The caps 634 may also be removed so as to allow for removal or replacement of the biasing elements 630.

Figure 11:
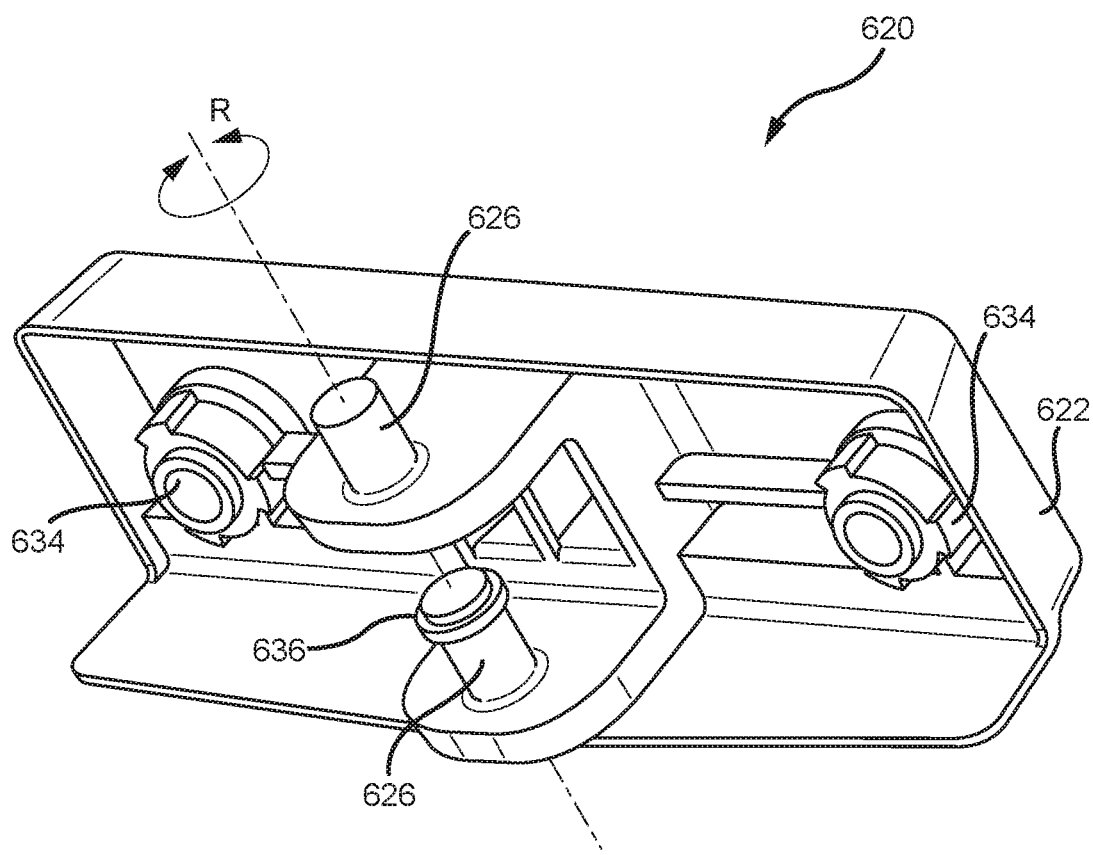
FIG. 11 is a bottom perspective view of a pivot mechanism for the breast compression paddle of FIG. 10A.
Figure 12:
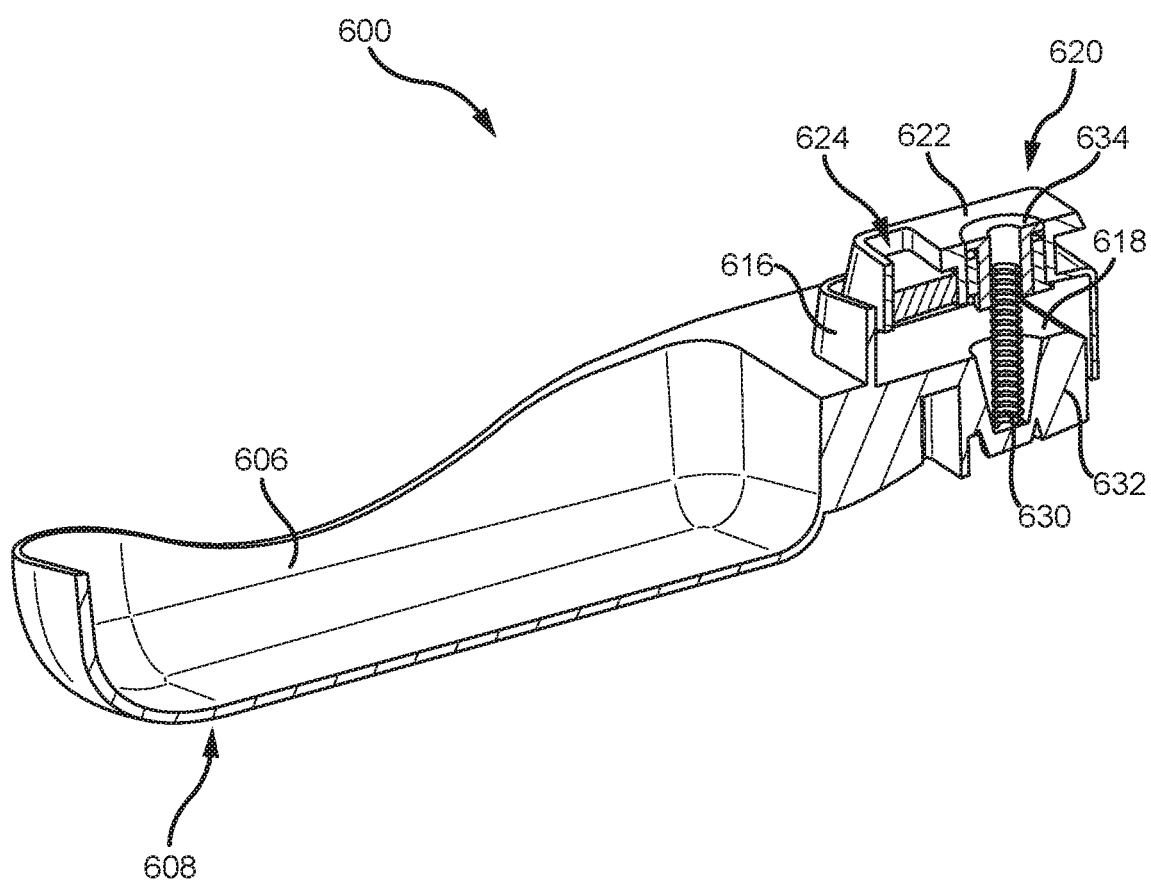
FIG. 12 is a perspective cross-sectional view of the breast compression paddle of FIG. 10A.

FIG. 11 is a bottom perspective view of a pivot mechanism 620 for the breast compression paddle 600 of FIG. 10A. FIG. 12 is a perspective cross-sectional view of the breast compression paddle 600 of FIG. 10A. A number of components are described above in FIGS. 10A-10C and are therefore not necessarily described further. In FIG. 11, two axles 626 are visible on an underside of the bracket 622. The axles 626 define the axis of rotation R about which the paddle 600 rotates. Either or both of the axles 626 may include a detent, protrusion, or other restraining element 636 that helps prevent inadvertent disengagement of the bracket 622 from the paddle 600. In an embodiment, the well 632 defines a shape so as to center the biasing element 630 therein, such as a frustoconical shape. The cap 634 at least partially receives a portion of the biasing element 630 so as to ensure alignment thereof.

FIGS. 13A-13E are cross-sectional views of embodiments of pivot mechanisms 700. Each of FIGS. 13A-13E include a paddle 702 supported below a pivot bracket 704 in a rest or neutral position. In the neutral position, the paddle 702 is substantially parallel to the bracket 704. The pivot bracket 704 includes one or more mounts 706 that allow the bracket 704 to be connected to a compression arm assembly. The bracket 704 includes at least one axle 708 that penetrates an opening 710 in the paddle 702, thus enabling pivoting movement or rotation R of the paddle 702 relative to the bracket 704. The paddle 702 includes a collar 712 that defines a receiver 718. The receiver 718 provides clearance between the paddle 702 and the bracket 704 and the collar 712 prevents pinching of, e.g., the fingers of a technician, as the paddle 702 rotates R. During imaging and/or biopsy procedures, a patient breast is placed in contact with a bottom surface 722 of the paddle 702, between the paddle 702 and a platform (not shown) of an imaging system. Due to the alignment of the breast relative to the paddle, size of the breast, densities of different portions thereof, or other factors, the paddle 702 is able to pivot or rotate R relative to the paddle 702. This can help reduce patient discomfort during compression. This rotation R is controlled, however, due to the presence of biasing elements 720 that urge the paddle 702 to the neutral position. Various biasing elements 720 are depicted in FIGS. 13A-13E.

Figure 13A:
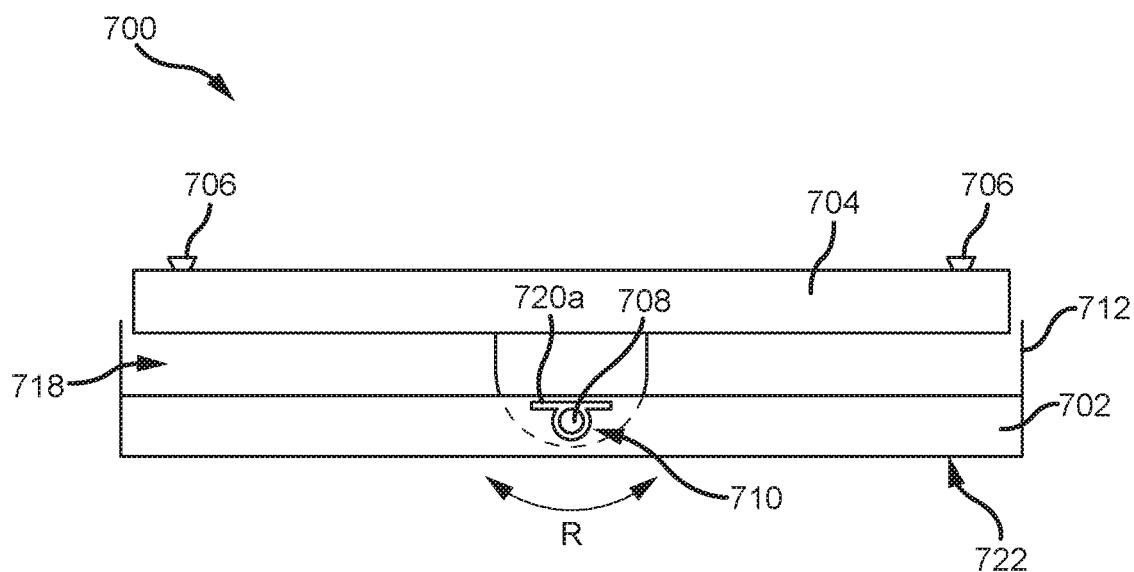
FIGS. 13A-13E are various views of embodiments of pivot mechanisms.
Figure 13B:
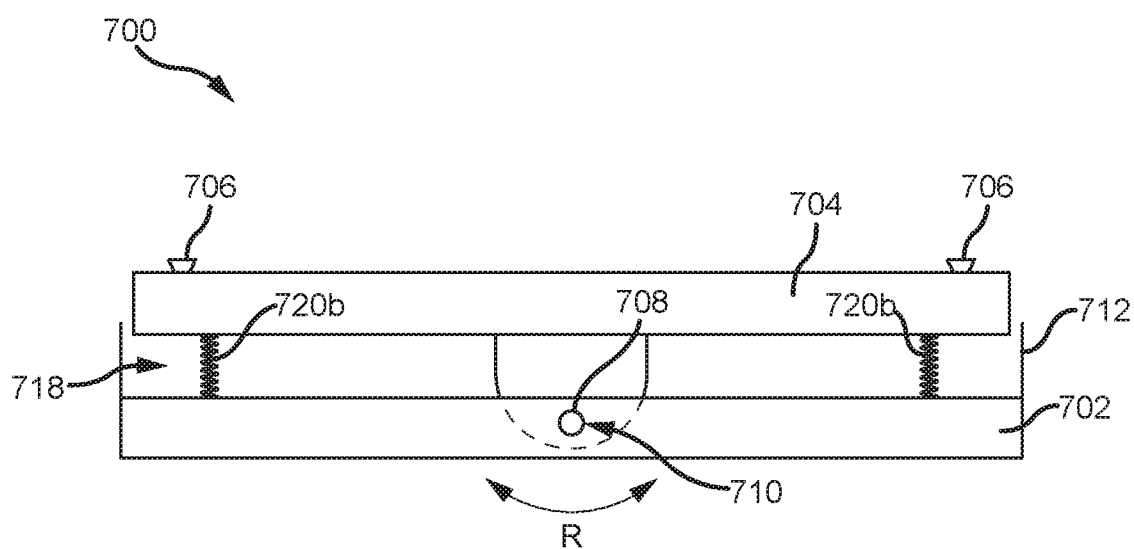
Figure 13C:
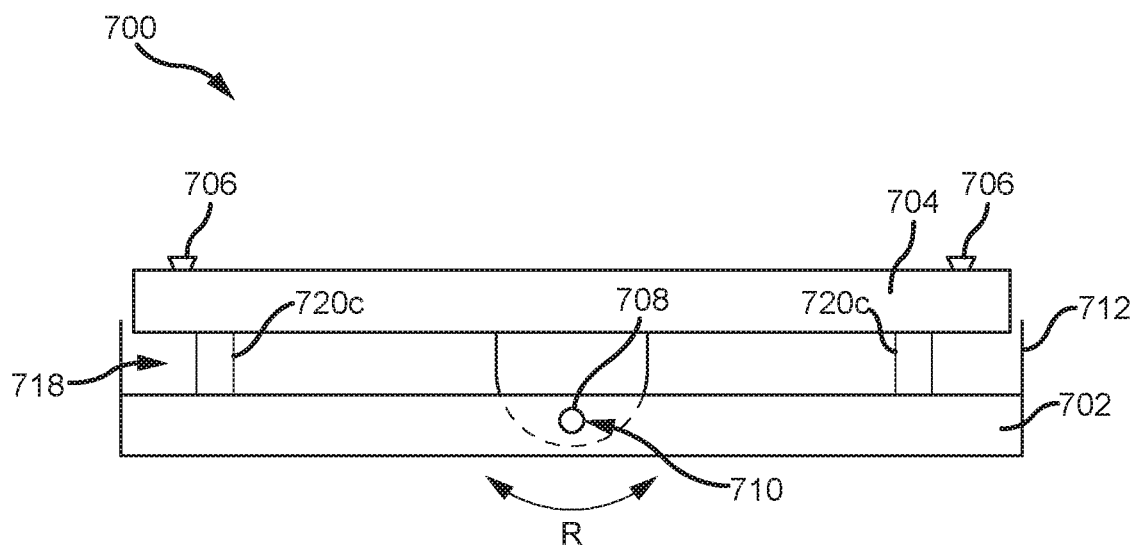
Figure 13D:
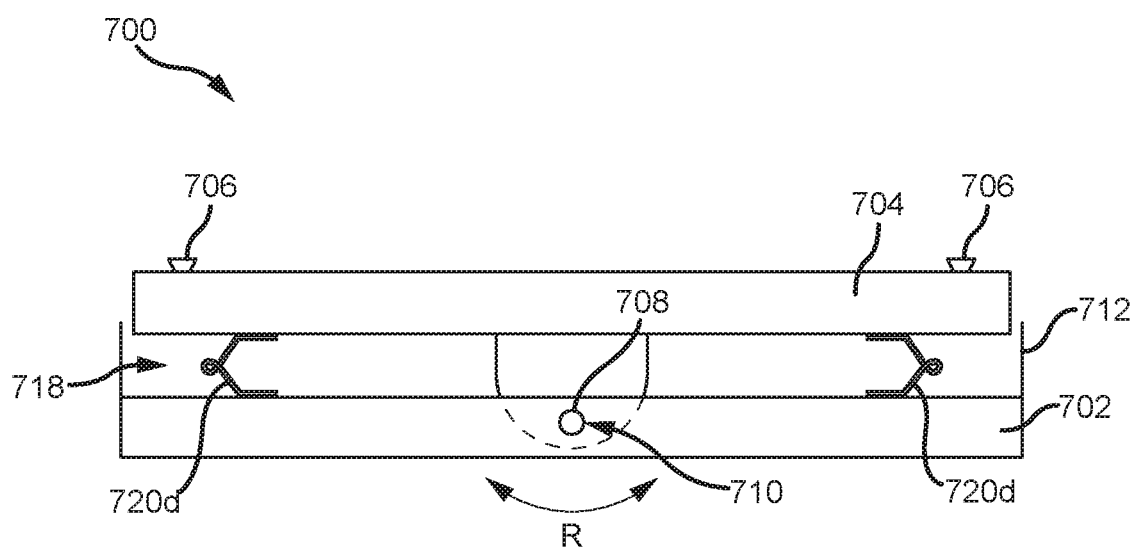
Figure 13E:
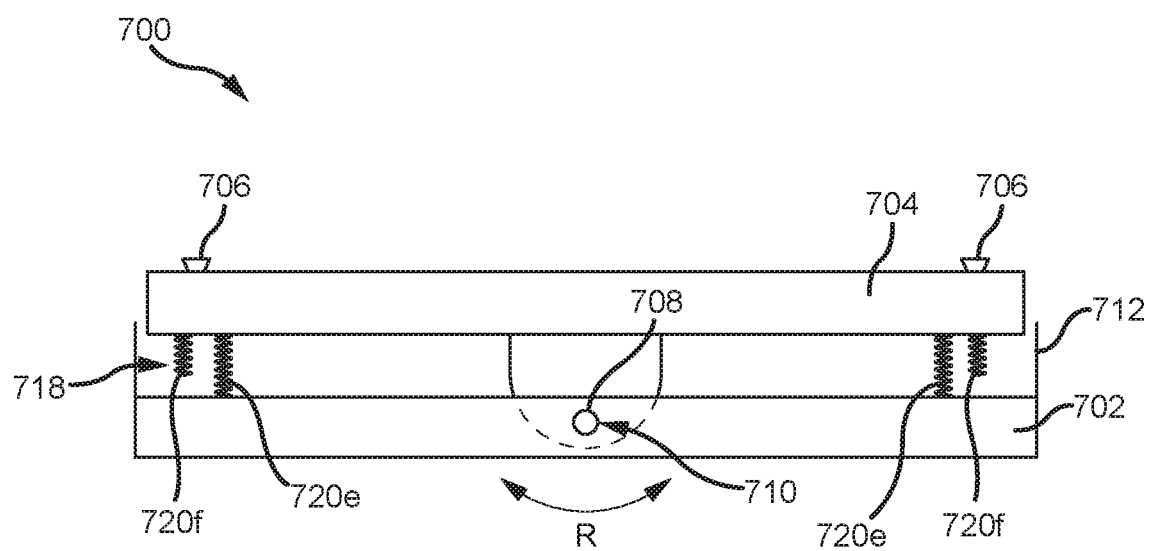

FIG. 13A depicts, for example, a torsion spring 720a disposed about the axle 708 that biases the paddle 702 towards the neutral position, regardless of which direction the paddle 702 pivots. FIG. 13B depicts a pair of biasing elements 720b in the form of coil springs, similar to the embodiment depicted in FIG. 10B. FIG. 13C depicts a pair of biasing elements 720c in the form of elastomer elements. FIG. 13D depicts a pair of biasing elements 720d in the form of leaf springs. Multiple pairs of biasing elements 720 can also be utilized. FIG. 13E depicts an embodiment where a first pair of biasing elements 720e constantly bias the paddle 702 into the neutral position. As the rotation R of the paddle 702 increases, however, the paddle 702 contacts a one of a second set of biasing elements 702f, which applies further biasing force against the paddle 702 as the rotational range increases. Although coil springs are depicted in FIG. 13E, other biasing elements, such as elastomer elements or leaf springs may be utilized. Additionally, the first pair of biasing elements 720e can be used in conjunction with a torsion spring such as the type depicted in FIG. 13A. In such a case, the torsion spring may only bias the paddle 702 during one range of rotation. Other configurations of biasing elements are contemplated. Additionally, the biasing elements may display either or both of constant or variable spring forces.

Figure 14:
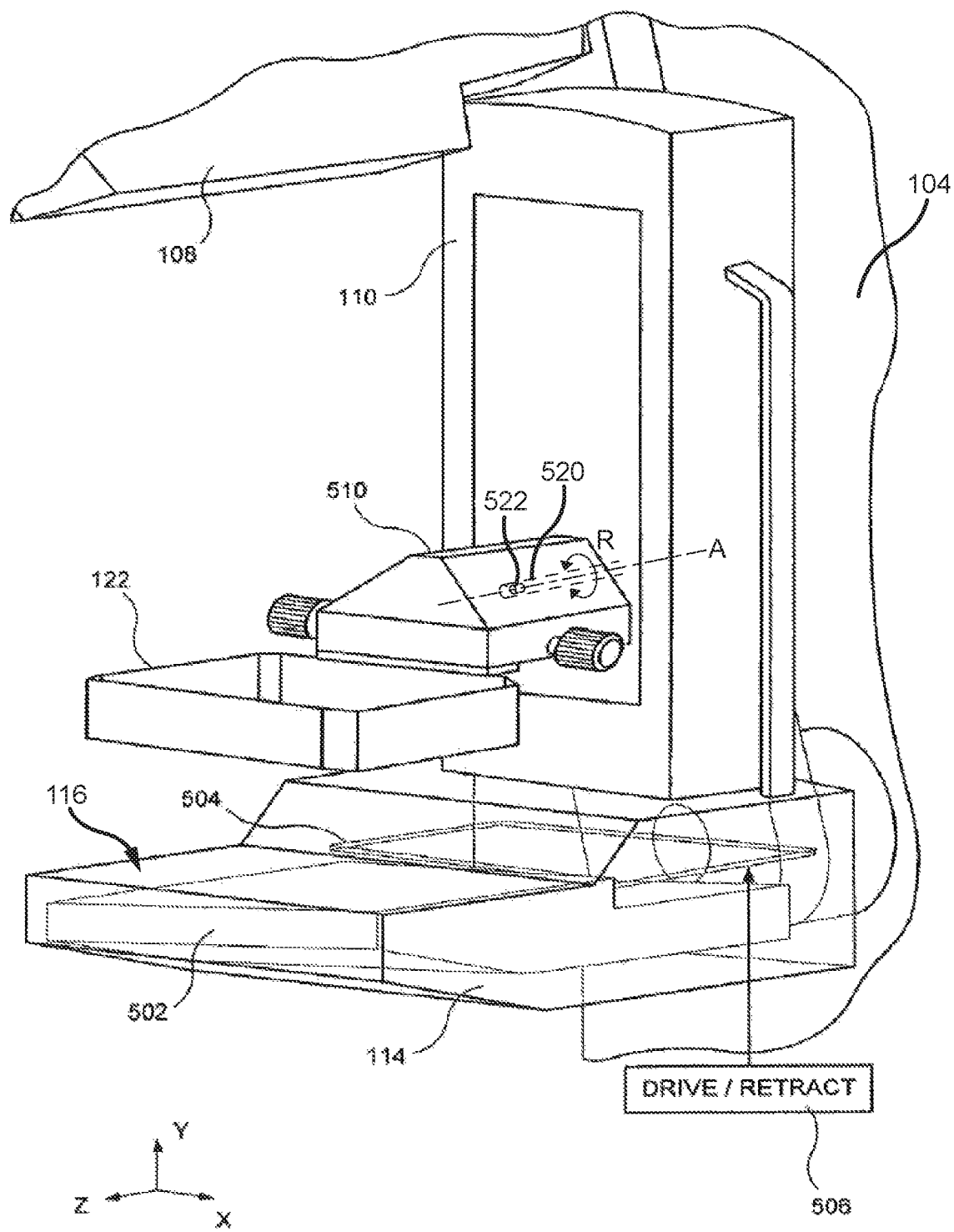
FIG. 14 is a perspective view of a compression arm assembly incorporating an embodiment of a pivot mechanism.

FIG. 14 is a perspective view of a compression arm assembly 110 that comprises a compression plate 122 and a receptor housing 114 having an upper surface 116 serving as a breast plate and enclosing a detector subsystem comprising a flat panel x-ray receptor 502, a retractable anti-scatter grid 504 and a mechanism 506 for driving and retracting anti-scatter grid 504. A power generation facility for x-ray tube assembly 108 may be included in an imaging arm assembly 104. A compression paddle 122 is removably mounted to a support 510 that moves up and down compression arm assembly 110 as needed for breast compression. A locking mechanism in the support 510 (not shown) can be used to maintain compression paddle 122 in place to prevent rotation. The locking mechanism can be manually set to a lock position, and manually unlocked by the operator, or can be controlled through an operator input. A sensor 522 can be included to sense whether compression paddle 122 is locked against pivoting, to provide information that work-station 102 can use for setting imaging protocols such as for automated breast compression and automated exposure methods. The sensor 522 can also determine the range of rotation of the support 510 during use or the position of the paddle 122 relative to the pivoting mechanism or axle 520. The sensor 522 can alternatively be incorporated into the pivoting paddles described above. The depicted embodiment includes an axle 520 connecting the support 510 to the compression arm assembly 110. The axle 520 enables rotation R about an axis A, as described above with regard to the pivoting paddles. Thus, the depicted system can utilize a generally fixed paddle 122 and incorporate rotational functionality into the compression arm assembly 110 itself, instead of into the paddle 122. Biasing elements such as those described above may be included so as to bias the support 510 into the depicted neutral position.

Figure 15:
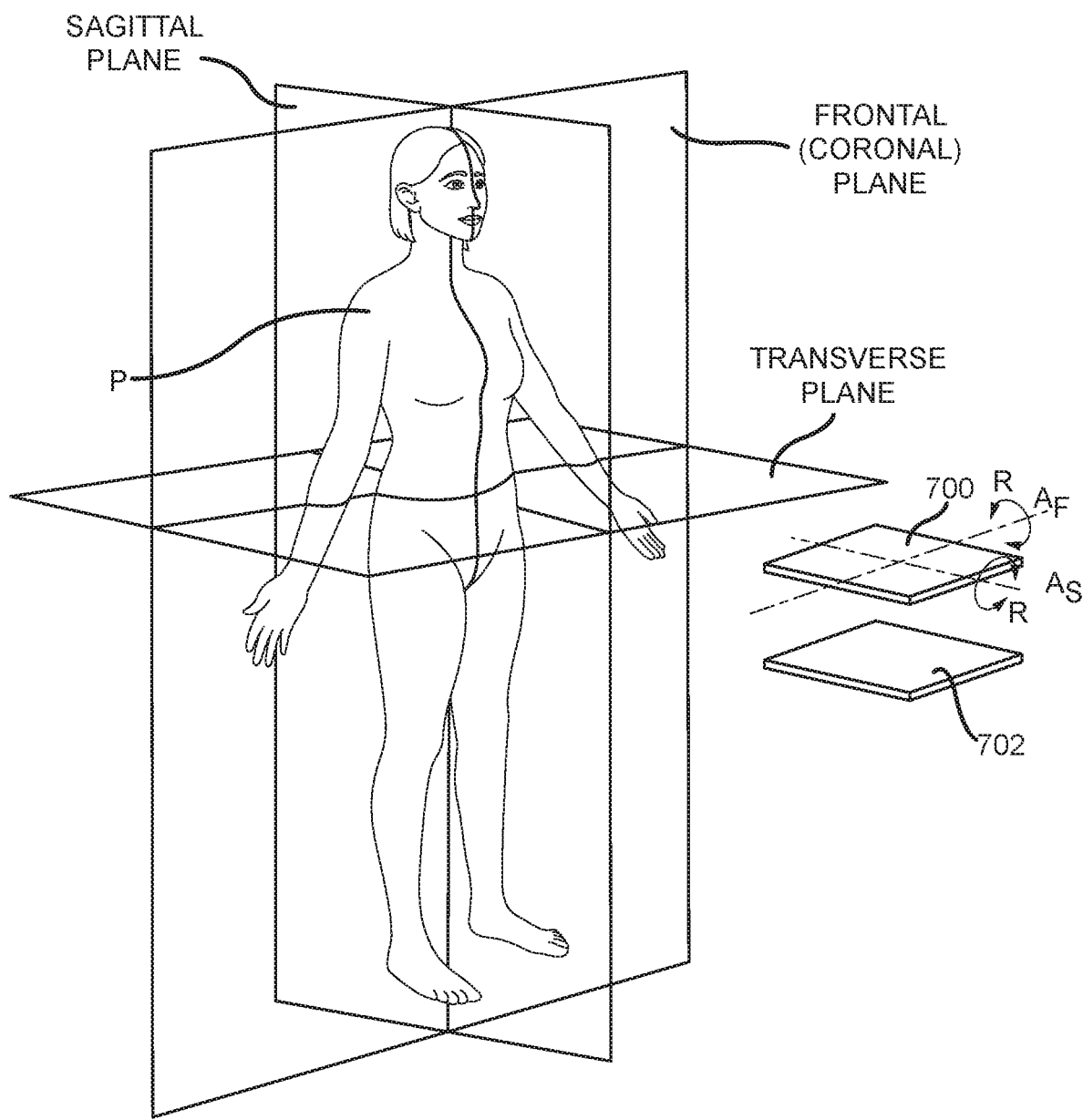
FIG. 15 is view of a pivoting breast compression paddle relative to a patient.

FIG. 15 is view of a pivoting breast compression paddle 700 relative to a patient P. A platform 702 supports the breast and remains substantially parallel to the transverse plane during imaging and biopsy procedures. Utilizing the technologies described herein, the paddle 700 may pivot or rotate R about an axis $A_S$ substantially parallel to the sagittal plane and substantially orthogonal to the coronal plane. Pivoting mechanisms incorporated into the paddle 700 or compression arm assembly may enable this functionality. Additionally, biasing mechanisms may be incorporated into the pivoting mechanism to control rotation as the breast is compressed by the paddle 700. Unlike systems that utilize pivoting mechanisms that require setting of a position of the paddle manually, the biased pivoting mechanisms described herein allow for responsive pivoting as compression increases, allowing for changes in breast density as compression is increased. Additionally, the paddle 700 may also be configured to pivot or rotate R about an axis $A_F$ substantially parallel to the coronal plane and substantially orthogonal to the sagittal plane. Thus, a wide variety of breast sizes, densities, shapes, etc., may be accommodated by a single, spring-biased system to lessen discomfort associated with breast compression. Maximum rotation about either axis $A_S$, $A_F$ can be limited by the amount of compression of the biasing elements used in the pivoting mechanisms. In certain embodiments, the paddle 700 can rotate up to about 2 degrees in either direction, up to about 4 degrees, up to about 8 degrees, and so on. Multiple pivoting mechanisms may be utilized in certain embodiments. For example, a pivoting mechanism such as that depicted in FIG. 9 may be utilized for rotation about axis $A_x$, while a pivoting mechanism such as that depicted in FIG. 14 may be utilized for rotation about Axis $A_y$. Alternatively, the pivoting mechanisms incorporated into the paddle (such as depicted in FIGS. 10A-10C) may be used in conjunction with the pivoting mechanism depicted in FIG. 9.

The above specific examples and embodiments are illustrative, and many variations can be introduced on these examples and embodiments without departing from the spirit of the disclosure or from the scope of the appended claims. For example, elements and/or features of different illustrative embodiments may be combined with each other and/or substituted for each other within the scope of this disclosure and appended claims.

What is claimed is:
1. A system comprising:
an imaging system housing;
an x-ray source connected to the imaging system housing for delivering energy to a breast of a patient;
a compression arm assembly housing connected to the imaging system housing;
a support connected to the compression arm assembly housing, wherein the support is configured to support the breast of the patient during delivery of the energy;

a detector disposed in the support, such that a surface of the support is disposed between the x-ray source and the detector, the detector adapted to receive the delivered energy from the x-ray source;

a paddle disposed between the support and the x-ray source, wherein a bottom surface of the paddle at least partially defines a plane, and wherein when in a rest position, the plane is substantially parallel to the support; and a bracket connecting the paddle to the compression arm assembly housing, wherein the bracket comprises a pivot mechanism comprising a first axle and an aligned second axle that define an axis of rotation substantially parallel to a sagittal plane of the patient, and wherein the pivot mechanism comprises at least one biasing element for biasing the paddle into the rest position, and wherein the first axle and the second axle are centrally disposed on the paddle.

2. The system of claim 1, wherein at least one biasing element comprises a pair of biasing elements.

3. The system of claim 2, wherein the bracket further comprises:

a pair of wells, each of the pair of wells receiving one of the pair of biasing elements; and a pair of caps, each of the pair of caps for closing one of the pair of wells.

4. The system of claim 1, wherein the at least one biasing element comprises a first pair of biasing elements and a second pair of biasing elements.

5. The system of claim 4, wherein the first pair of biasing elements biases the paddle during a first range of rotation and wherein the second pair of biasing elements biases the paddle during a second range of rotation.

6. The system of claim 4, wherein one of the first pair of biasing elements contacts the paddle during a first range of rotation and a second range of rotation, and wherein one of the second pair of biasing elements contacts the paddle only during a second range of rotation.

7. The system of claim 1, wherein the pivot mechanism further defines an axis of rotation substantially parallel to the coronal plane of the patient.

8. The system of claim 1, wherein the at least one biasing element comprises at least one of a constant-force biasing element and a variable-force biasing element.

9. The system of claim 1, wherein the paddle comprises a collar at least partially defining a receiver for receiving the bracket.

10. The system of claim 1, further comprising a sensor for detecting a position of the paddle relative to the pivot mechanism.

* * * * *